US008067459B2

(12) United States Patent
Ashwell et al.

(10) Patent No.: US 8,067,459 B2
(45) Date of Patent: Nov. 29, 2011

(54) LAPACHONE COMPOUNDS AND METHODS OF USE THEREOF

(75) Inventors: Mark Ashwell, Carlisle, MA (US); Manish Tandon, Framingham, MA (US); Jean-Marc Lapierre, Pelham, NH (US); Syed Ali, North Andover, MA (US); Yanbin Liu, Acton, MA (US); Chiang J. Li, Cambridge, MA (US)

(73) Assignee: ArQule, Inc., Woburn, MA (US)

( * ) Notice: Subject to any disclaimer, the term of this patent is extended or adjusted under 35 U.S.C. 154(b) by 550 days.

(21) Appl. No.: 12/252,681

(22) Filed: Oct. 16, 2008

(65) Prior Publication Data

US 2009/0176801 A1     Jul. 9, 2009

Related U.S. Application Data

(60) Provisional application No. 60/999,294, filed on Oct. 16, 2007.

(51) Int. Cl.
*A61K 31/39* (2006.01)
*C07D 327/02* (2006.01)
(52) U.S. Cl. ............. 514/431; 514/434; 549/10; 549/16
(58) Field of Classification Search .................... 549/16, 549/10; 514/434, 431
See application file for complete search history.

(56) References Cited

U.S. PATENT DOCUMENTS

| | | | | |
|---|---|---|---|---|
| 5,763,625 | A | 6/1998 | Boothman et al. | 549/390 |
| 5,824,700 | A | 10/1998 | Frydman et al. | 514/454 |
| 5,969,163 | A | 10/1999 | Frydman et al. | 549/389 |
| 6,245,807 | B1 | 6/2001 | Pardee et al. | 514/454 |
| 2002/0169135 | A1 | 11/2002 | Pardee et al. | 514/27 |
| 2003/0091639 | A1 | 5/2003 | Jiang et al. | 424/486 |
| 2004/0071775 | A1 | 4/2004 | Jiang et al. | 424/486 |

FOREIGN PATENT DOCUMENTS

| | | |
|---|---|---|
| WO | WO 94/04145 | 3/1994 |
| WO | WO 00/61142 | 10/2000 |
| WO | WO 03/011224 A2 | 2/2003 |
| WO | WO 2004/045557 * | 6/2004 |
| WO | WO 2004/045557 A2 | 6/2004 |
| WO | WO 2007/139569 A1 | 12/2007 |

OTHER PUBLICATIONS

Banker and Rhodes, Modern Pharmaceutics, 2007, Marcel Dekker, Inc, 3rd Edition, p. 596.*
'Cancer Prevention Overview', http://www.cancer.gov/cancertopics/pdq/prevention/overview/patient, accessed Apr. 9, 2010.*
Golub et al., Molecular Classification of Cancer: Class Discovery and Class Prediction by Gene Expression Monitoring. Science, vol. 286, Oct. 15, 1999, p. 531-537.*
'Metabolite', http://www.encyclopedia.com/doc/1E1-metabolit.html, accessed Jan. 25, 2008.*
'Prodrug', http://www.medterms.com/script/main/art.asp?articlekey=23992, accessed Apr. 8, 2011.*
Target Cancer Therapies, http://www.cancer.gov/cancertopics/factsheet/therapy/targeted,a accessed Jan. 12, 2011.*
Voskoglou-Nomikos et al, Clincial Predictive Value of the in Vitro Cell line, Human Xenograft, and Mouse Allograft Preclinical Cancer Models, Sep. 15, 2003, Clnical Cancer Research, vol. 9, p. 4227-4239.*
Pérez-Sacau et al., "Synthesis and pharmacophore modeling of naphthoquinone derivatives with Cytotoxic activity in human promyelocytic leukemia HL-60 cell line", *J. Med. Chem.*, 50(4):696-706 (2007).
Chuang et al., "Oxidative Free Radical Reaction of 2-Phenylthio-1,4-Naphthoquinones Initiated by Manganese(III) Acetate", *Heterocycles*, 43(10):2215-2221 (1996).
Goncalves et al., "Evaluation of the Toxicity of 3-Allyl-β-Lapachone against Trypanosoma Cruzi Bloodsteam Forms", *Molecular and Biochemical Parasitology*, 1:167-176 (1980).
Huang et al., "β-Lapachone Induces Cell Cycle Arrest and Apoptosis in Human Colon Cancer Cells" *Molecular Medicine*, 5:711-720 (1999).
Klapars et al., "Copper-Catalyzed Halogen Exchange in Aryl Halides: An Aromatic Finkelstein Reaction", *J. Am. Chem. Soc.*, 124:14844-14845 (2002).
Krapcho et al., "Heterosubstituted Anthracene-9,10-dione Analogues. The Synthesis and Antitimor Evaluation of 5,8-Bis[(aminoalkyl)amino]naptho[2,3-b]thiopene-4,9-diones", *J. Med. Chem.*, 33:2651-2655 (1990).
Kurokawa, "The Reaction of Cadalene and Eudalene with Sulfur", *Bulletin of the Chemical Society of Japan*, 43:1454-1459 (1970).
Lai et al., "β-Lapachone Induced Cell Death in Human Hepatoma (HepA2) Cells", *Histol Histophatol*, 13:89-97 (1998).
Li et al., "Induction of Apoptosis by β-Lapachone in Human Prostate Cancer Cells", *Cancer Research*, 55:3712-3715 (1995).
Li et al., "Potent Induction of Apoptosis by β-Lapachone in Human Multiple Myeloma Cell Lines and Patient Cells", *Molecular Medicine*, 6(12):1008-1015 (2000).
Li et al., "Potent Inhibition of Tumor Survival in vivo by β-Lapachone Plus Taxol: Combining Drugs Imposes Different Artificial Checkpoints", *PNAS*, 96:13369-13374 (1999).
Li et al., "Release of Mitochondrial Cytochrome C in both Apoptosis and Necrosis Induced by β-Lapachone in Human Carcinoma Cells", *Molecular Medicine*, 5:232-239 (1999).
Li et al., "Selective Killing of Cancer Cells by β-Lapachone: Direct Checkpoint Activation as a Strategy against Cancer", *PNAS*, 100(5):2674-2678 (2003).
Li et al., "β-Lapachone, a Novel DNA Topoisomerase I Inhibitor with a Mode of Action Different from Camptothecin", *The Journal of Biological Chemistry*, 268(30):22463-22468 (1993).
Planchon et al., "β-Lapachone-Mediated Apoptosis in Human Promyelocytic Leukemia (HL-60) and Human Prostate Cancer Cells: A p53-independent Response", *Cancer Research*, 55:3706-3711 (1995).

(Continued)

*Primary Examiner* — Taylor V Oh
*Assistant Examiner* — Karen Cheng
(74) *Attorney, Agent, or Firm* — Mintz Levin Cohn Ferris Glovsky and Popeo, P.C.; Ivor R. Elrifi, Esq.; Matthew Pavao, Esq.

(57) ABSTRACT

The invention provides lapachone analogs and derivatives as well as methods of use thereof. These compounds can be used in pharmaceutical compositions for the treatment or prevention of cell proliferation disorders. These compounds can also be used in the treatment or prevention of cancer or precancerous conditions.

57 Claims, No Drawings

OTHER PUBLICATIONS

Portela et al., "Redox Cycling of β-Lapachone and Related o-Naphthoquinones in the Presence of Dihydrolipoamide and Oxygen", *Biochemical Pharmacology*, 51:275-283 (1996).

Prieto et al., "Arylboronic Acids and Arylpinacolboronate Esters in Suzuki Coupling Reactions Involving Indoles. Partner Role Swapping and Heterocycle Protection", *J. Org. Chem.*, 69:6812-6820 (2004).

Schaffner-Sabba et al., "β-Lapachone: Synthesis of Derivatives and Activities in Tumor Models", *J. Med. Chem.*, 27:990-994 (1984).

Suginome et al., "One-Step Synthesis of 2,3-Dihydronaphtho[2,3-b]thiophene-4,9-diones by a New Regioselective [3+2] Photoaddition of Photogenerated 2-Mercapto-1,4-naphthoquinone with Alkenes", *J. Chem. Soc., Chem. Commun.*, 807-809 (1993).

Tapia et al., "Synthesis of 2H-Naphtho[2,3-b]Thiopyranoquinones and Density Functional Study for the Diels-Alder Reaction of a Benzothiopyranoquinone", *Heterocycles*, 53(3):585-598 (1999).

Tapia et al., "Synthesis of 3,4-Dihydro-4-hydroxy-9-methoxy-2H-naphtho[2,3-b]thiopyranoquinone", *Tetrahedron Letters*, 38(1):153-154 (1997).

Tonholo et al., "Electrochemical Properties of Biologically Active Heterocyclic Naphthoquinones", *J. Braz. Chem. Soc.*, 9(2):163-169 (1998).

Weller et al., "Topoisomerase-I Inhibitors for Human Malignant Glioma: Differential Modulation of p53, p21, bax and bcl-2 Expression and of CD95-Mediated Apoptosis by Camptothecin and β-Lapachone", *Int. J. Cancer*, 73:707-714 (1997).

Wuerzberger et al., "Induction of Apoptosis in MCF-7:WS8 Breast Cancer Cells by β-Lapachone", *Cancer Research*, 58:1876-1885 (1998).

Sugiyama et al., "Aldose reductase catalyzed the oxidation of naphathalene-1,2-dihydrodiol for the formation of ortho-naphthoquinone", *Drug Metab. Disposition*, 27(1):60-67 (1999).

\* cited by examiner

LAPACHONE COMPOUNDS AND METHODS OF USE THEREOF

CROSS-REFERENCE TO RELATED APPLICATIONS

This application claims priority to, and the benefit of, U.S. Patent Application No. 60/999,294 filed Oct. 16, 2007, the contents of which are incorporated herein by reference in their entirety.

BACKGROUND OF THE INVENTION

β-lapachone (3,4-dihydro-2,2-dimethyl-2H-naphtho[1,2-b]pyran-5,6-dione), a quinone, is derived from lapachol (a naphthoquinone) which can be isolated from the lapacho tree (*Tabebuia avellanedae*), a member of the catalpa family (Bignoniaceae). Lapachol and β-lapachone (with numbering) have the following chemical structures:

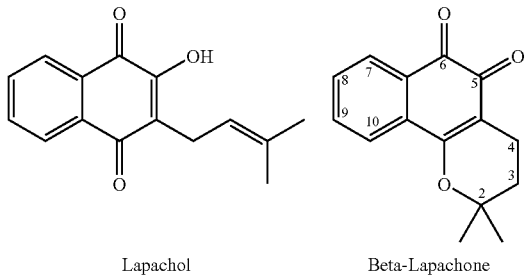

Lapachol                Beta-Lapachone

β-lapachone, as well as its intermediates, derivatives and analogs thereof, are described in Li, C. J. et al., (1993) *J. Biol. Chem.*, 268(30): 22463-22468. As a single agent, β-lapachone has demonstrated significant antineoplastic activity against human cancer cell lines at concentrations typically in the range of 1-10 μM ($IC_{50}$). Cytotoxicity has been demonstrated in transformed cell lines derived from patients with promyelocytic leukemia (Planchon et al., (1996) *Cancer Res.*, 55: 3706-3711), prostate (Li, C. J., et al., (1995) *Cancer Res.*, 55: 3712-3715), malignant glioma (Weller, M. et al., (1997) *Int. J. Cancer*, 73: 707-714), hepatoma (Lai, C. C., et al., (1998) *Histol Histopathol*, 13: 89-97), colon (Huang, L., et al., (1999) *Mol Med*, 5: 711-720), breast (Wuertzberger, S. M., et al., (1998) *Cancer Res.*, 58: 1876), ovarian (Li, C. J. et al., (1999) *Proc. Natl. Acad. Sci. USA*, 96(23): 13369-13374), pancreatic (Li, Y., et al., (2000) *Mol Med*, 6: 1008-1015; Li, Y., (1999) *Mol Med*, 5: 232-239), and multiple myeloma cell lines, including drug-resistant lines (Li, Y., (2000) *Mol Med*, 6: 1008-1015). No cytotoxic effects were observed on normal fresh or proliferating human PBMC (Li, Y., (2000) *Mol Med*, 6: 1008-1015).

β-lapachone appears to work by inducing unscheduled expression of checkpoint molecules, e.g. E2F, independent of DNA damage and cell cycle stages. Several studies have shown that β-lapachone activates the E2F1 checkpoint pathway and induces cell death in cancer cells from a variety of tissues without affecting normal cells from these tissues (U.S. Patent Application Publication No. 2002/0169135, incorporated by reference herein). In normal cells with their intact regulatory mechanisms, such an imposed expression of a checkpoint molecule results in a transient expression pattern and causes little consequence. In contrast, cancer and pre-cancer cells have defective mechanisms, which result in unchecked and persistent expression of unscheduled checkpoint molecules, e.g. E2F1, leading to selective cell death in cancer and pre-cancer cells.

In addition to β-lapachone, a number of β-lapachone analogs having antiproliferative properties have been disclosed in the art, such as those described in PCT International Application PCT/US93/07878 (WO94/04145), which is incorporated by reference herein, and U.S. Pat. No. 6,245,807, incorporated by reference herein, in which a variety of substituents may be attached at positions 3- and 4- on the β-lapachone compound. PCT International Application PCT/US00/10169 (WO 00/61142), incorporated by reference herein, discloses β-lapachone, which may have a variety of substituents at the 3-position as well as in place of the methyl groups attached at the 2-position. U.S. Pat. Nos. 5,763,625, 5,824,700, and 5,969,163, each of which is incorporated by reference herein, disclose analogs and derivatives with a variety of substituents at the 2-, 3- and 4-positions. Furthermore, a number of journals report β-lapachone analogs and derivatives with substituents at one or more of the following positions: 2-, 3-, 8- and/or 9-positions, (See, Sabba et al., (1984) *J Med Chem* 27:990-994 (substituents at the 2-, 8- and 9-positions); (Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions)).

Moreover, U.S. Patent Application Publication No. 2004/0266857 and PCT International Application PCT/US2003/037219 (WO 04/045557), incorporated in by reference herein, disclose and several journal reports describe structures having sulfur-containing hetero-rings in the "α" and "β" positions of lapachone (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2):163-169; and Krapcho A P et al., (1990) *Journal of Medicinal Chemistry* 33(9):2651-2655). These findings encourage the design and synthesis of new lapachone derivatives and analogs and their evaluation for antiproliferative activity in a variety of biological systems.

SUMMARY OF THE INVENTION

The present invention provides the compounds of Formula I:

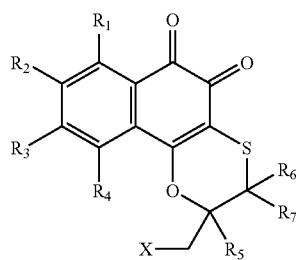

or a pharmaceutically acceptable salt and/or an individual diastereomer thereof, wherein:

$R_1$, $R_2$, $R_3$, and $R_4$ are each, independently, H, halogen, hydroxyl, unsubstituted or substituted $C_1$-$C_6$ alkyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, or amide;

$R_5$ is H or carboxyacid or carboxy esters;

$R_6$ and $R_7$ are each, independently, H, unsubstituted or substituted $C_1$-$C_6$ alkyl, unsubstituted or substituted $C_1$-$C_6$ alkenyl, unsubstituted and substituted $C_1$-$C_6$ alkoxy, unsubstituted or substituted $C_1$-$C_6$ acyl, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle;

X is H, —$OR_a$, unsubstituted or substituted alkylamino; unsubstituted or substituted dialkylamino, or substituted heterocycle;

$R_a$ is H, unsubstituted or substituted amide, unsubstituted or substituted heterocycle, or substituted silyl; provided that if X is —$OR_a$ and Ra and $R_1$-$R_5$ are all H, then $R_6$ and $R_7$ are not both H;

if X and $R_1$-$R_6$ are all H, then $R_7$ is not methyl; and if X, $R_1$-$R_5$ and $R_7$ are all H, then $R_6$ is not methyl.

The present invention also provides the compounds of Formula II:

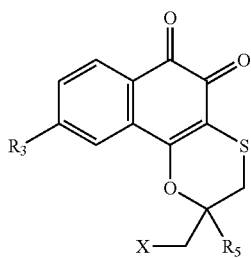

(II)

or a pharmaceutically acceptable salt and/or an individual diastereomer thereof, wherein:

$R_3$ is H, halogen, unsubstituted or substituted aryl, unsubstituted or substituted phenyl, unsubstituted or substituted heteroaryl, or unsubstituted or substituted heterocycle;

$R_5$ is H or carboxyacid or carboxy esters;

X is H, —$OR_a$, unsubstituted or substituted alkylamino; unsubstituted or substituted dialkylamino, or substituted heterocycle;

$R_a$ is H, unsubstituted or substituted amide, unsubstituted or substituted heterocycle, or substituted silyl; provided that if X is —$OR_a$ and Ra and $R_1$-$R_5$ are all H, then $R_6$ and $R_7$ are not both H;

if X and $R_1$-$R_6$ are all H, then $R_7$ is not methyl; and if X, $R_1$-$R_5$ and $R_7$ are all H, then $R_6$ is not methyl.

Compounds of Formula I and II include those in which, X is a H or substituted heterocycle. The heterocycle can be piperazine or piperidine. The heterocycle can be substituted with carbonylalkoxy; carboxyacid; phenyl; heteroaryl; heterocycle; hydroxyl; acetal; $C_1$-$C_6$ alkyl, each of which may be substituted. The heterocycle can be substituted at the 4-position.

The heterocycle can be substituted with carbonylalkoxy. In one embodiment, the carbonylalkoxy is

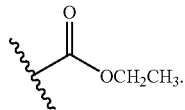

The heterocycle can be substituted with hydroxyl.

The heterocycle can be substituted with substituted $C_1$-$C_6$ straight chain alkyl. The substituted $C_1$-$C_6$ straight chain alkyl can be —$CH_2W$. W can be hydroxyl, alkoxy, or —C(O)$NR_8R_9$. $R_8$ can be H or $C_1$-$C_6$ straight chain alkyl and $R_9$ can be $C_1$-$C_6$ straight chain alkyl, $C_3$-$C_6$ branched alkyl, $C_3$-$C_6$ cycloalkyl. In one embodiment, W is hydroxyl or —C(O)$NR_8R_9$. For example, $R_8$ is H and $R_9$ is isopropyl.

The heterocycle can be substituted with substituted phenyl. The phenyl can be substituted with at least one halogen. For example, the phenyl is substituted with F.

The heterocycle can be substituted with acetal. For example, the acetal is cyclic acetal.

Compounds of Formula I and II include those in which, X is —$OR_a$. $R_a$ can be a substituted amide. The substituted amide can be —C(O)$NR_{10}R_{11}$. $R_{10}$ and $R_{11}$ are the same or different from each other and each can be H; unsubstituted or substituted phenyl; unsubstituted or substituted aryl; methyl; unsubstituted or substituted $C_2$-$C_6$ straight chain alkyl; unsubstituted or substituted $C_3$-$C_6$ branched alkyl; unsubstituted or substituted $C_3$-$C_8$ cycloalkyl; unsubstituted or substituted $C_3$-$C_6$ alkenyl; unsubstituted or substituted heterocycle; or unsubstituted or substituted heteroaryl. In one embodiment, $R_{10}$ is H and $R_{11}$ is a substituted or unsubstituted phenyl or $C_3$-$C_6$ branched alky. The phenyl can be substituted with halogen, hydroxyl, methyl, —$CF_3$, $C_2$-$C_6$ straight chain alkyl, $C_3$-$C_6$ branched alkyl, $C_3$-$C_8$ cycloalkyl, nitro, cyano, amino, alkylamino, dialkylamino, alkoxy, —$OCF_3$, carboxyacid, carbonylalkyl, carbonylalkoxy, thio, thioalkyl, phenyl, aryl, heterocycle, or heteroaryl. For example, the phenyl is substituted with halogen, hydroxyl, —$CF_3$, nitro, cyano, or alkoxy. In another example, the phenyl is substituted with at least one halogen. For example, the halogen is F. In another example, the branched alkyl is isopropyl.

$R_a$ can also be $R^xR^yR^zSi$—. $R^x$, $R^y$, and $R^z$ can be the same as or different from each other and each represents methyl, ethyl, i-propyl, t-butyl, or phenyl. In one embodiment, $R^x$ and $R^y$ are both phenyl and $R^z$ is t-butyl.

$R_a$ can also be unsubstituted or substituted heterocycle. For example, the heterocycle is pyridine. For example, the pyridine is 3-pyridine.

Compounds of Formula I and II include those in which, $R_3$ is H, unsubstituted or substituted phenyl or unsubstituted or substituted heterocycle. In one embodiment, $R_3$ is unsubstituted phenyl or heterocycle. For example, the heterocycle is piperidine.

Preferred compounds of Formula I and II are those in which, X is alkylamino or dialkylamino, each which may be substituted. The alkylamino or dialkylamino can be —$NR_{12}R_{13}$. $R_{12}$ and $R_{13}$ are each independently H, unsubstituted or substituted $C_1$-$C_6$ straight chain alkyl, $C_3$-$C_6$ branched alkyl, or unsubstituted or substituted benzyl. $R_{12}$ can be substituted with $C_1$-$C_6$ straight chain alkyl. The alkyl can be substituted with acetal. $R_{13}$ can be ethylphenyl or methyl. In one embodiment, $R_{12}$ is H and $R_{13}$ is unsubstituted benzyl or substituted $C_1$-$C_6$ straight chain alkyl.

Compounds of Formula I and II include those in which, $R_5$ and X are both H.

The present invention also provides the compounds of Formula III:

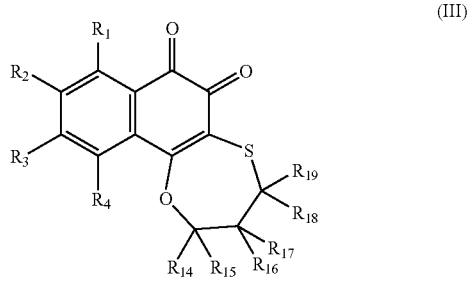

(III)

or a pharmaceutically acceptable salt and/or an individual diastereomer thereof, wherein:

wherein $R_1$, $R_2$, $R_3$, $R_4$, $R_{14}$, $R_{15}$, $R_{16}$, $R_{17}$, $R_{18}$, and $R_{19}$ are each, independently, H, halogen, hydroxyl, unsubstituted or substituted $C_1$-$C_6$ alkyl, unsubstituted or substituted $C_1$-$C_6$ alkenyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, amide, unsubstituted or substituted $C_1$-$C_6$ acyl, $C_1$-$C_6$ alkoxycarbonyl, amino, alkylamino, or dialkylamino.

The present invention also provides pharmaceutical compositions comprising a compound of Formula I, II or III in combination with a pharmaceutically acceptable carrier. Preferably, the compound of Formula I, II or III is in a therapeutically effective amount.

The present invention also provides a method of treating or preventing cell proliferative disorders comprising administering to a mammal in need thereof a therapeutically effective amount of a compound of Formula I, II or III.

The present invention also provides a method of treating cancer or precancerous conditions or preventing cancer comprising administering to a mammal in need thereof a therapeutically effective amount of a compound of Formula I, II or III.

The present invention also provides methods for the synthesis of compounds of Formula I, II or III.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In the case of conflict, the present specification, including definitions, will control. In addition, the materials, methods, and examples are illustrative only and are not intended to be limiting.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention provides novel tricyclic dihydrooxathiine naphthoquinone derivatives, a synthetic method for making the derivatives, and the use of the derivatives to inhibit neoplastic cell proliferation. The naphthoquinone derivatives of the present invention are related to the compounds known as β-lapachone (3,4-dihydro-2,2-dimethyl-2H-naphtho(1,2-b)pyran-5,6-dione), The structure of β-lapachone is described above. The β-lapachone analogs of the present invention include oxathiine hetero-rings.

The present invention provides the compounds of Formula I:

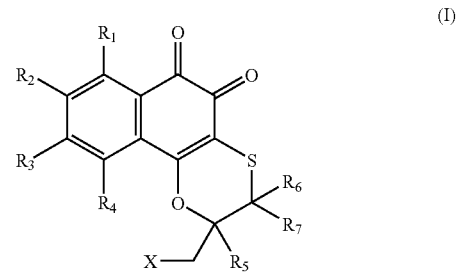

(I)

or a pharmaceutically acceptable salt and/or an individual diastereomer thereof, wherein:

$R_1$, $R_2$, $R_3$, and $R_4$ are each, independently, H, halogen, hydroxyl, unsubstituted or substituted $C_1$-$C_6$ alkyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, or amide;

$R_5$ is H or carboxyacid or carboxy esters;

$R_6$ and $R_7$ are each, independently, H, unsubstituted or substituted $C_1$-$C_6$ alkyl, unsubstituted or substituted $C_1$-$C_6$ alkenyl, unsubstituted and substituted $C_1$-$C_6$ alkoxy, unsubstituted or substituted $C_1$-$C_6$ acyl, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle;

X is H, —$OR_a$, unsubstituted or substituted alkylamino; unsubstituted or substituted dialkylamino, or substituted heterocycle;

$R_a$ is H, unsubstituted or substituted amide, unsubstituted or substituted heterocycle, or substituted silyl; provided that if X is —$OR_a$ and Ra and $R_1$-$R_5$ are all H, then $R_6$ and $R_7$ are not both H;

if X and $R_1$-$R_6$ are all H, then $R_7$ is not methyl; and if X, $R_1$-$R_5$ and $R_7$ are all H, then $R_6$ is not methyl.

The present invention also provides the compounds of Formula II:

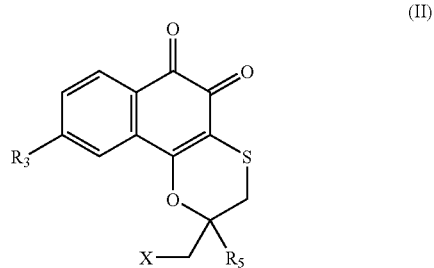

(II)

or a pharmaceutically acceptable salt and/or an individual diastereomer thereof, wherein:

$R_3$ is H, halogen, unsubstituted or substituted aryl, unsubstituted or substituted phenyl, unsubstituted or substituted heteroaryl, or unsubstituted or substituted heterocycle;

$R_5$ is H or carboxyacid or carboxy esters;

X is H, —$OR_a$, unsubstituted or substituted alkylamino; unsubstituted or substituted dialkylamino, or substituted heterocycle;

$R_a$ is H, unsubstituted or substituted amide, unsubstituted or substituted heterocycle, or substituted silyl; provided that if X is —$OR_a$ and Ra and $R_1$-$R_5$ are all H, then $R_6$ and $R_7$ are not both H;

if X and $R_1$-$R_6$ are all H, then $R_7$ is not methyl; and if X, $R_1$-$R_5$ and $R_7$ are all H, then $R_6$ is not methyl.

Compounds of Formula I and II include those in which, X is a H or substituted heterocycle. The heterocycle can be piperazine or piperidine. The heterocycle can be substituted with carbonylalkoxy; carboxyacid; phenyl; heteroaryl; heterocycle; hydroxyl; acetal; $C_1$-$C_6$ alkyl, each of which may be substituted. The heterocycle can be substituted at the 4-position.

The heterocycle can be substituted with carbonylalkoxy. In one embodiment, the carbonylalkoxy is

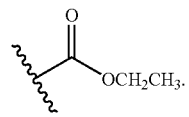

The heterocycle can be substituted with hydroxyl.

The heterocycle can be substituted with substituted $C_1$-$C_6$ straight chain alkyl. The substituted $C_1$-$C_6$ straight chain alkyl can be —$CH_2W$. W can be hydroxyl, alkoxy, or —$C(O)NR_8R_9$. $R_8$ can be H or $C_1$-$C_6$ straight chain alkyl and $R_9$ can be $C_1$-$C_6$ straight chain alkyl, $C_3$-$C_6$ branched alkyl, $C_3$-$C_6$ cycloalkyl. In one embodiment, W is hydroxyl or —$C(O)NR_8R_9$. For example, $R_8$ is H and $R_9$ is isopropyl.

The heterocycle can be substituted with substituted phenyl. The phenyl can be substituted with at least one halogen. For example, the phenyl is substituted with F.

The heterocycle can be substituted with acetal. For example, the acetal is cyclic acetal.

Compounds of Formula I and II include those in which, X is —$OR_a$. $R_a$ can be a substituted amide. The substituted amide can be —$C(O)NR_{10}R_{11}$. $R_{10}$ and $R_{11}$ are the same or different from each other and each can be H; unsubstituted or substituted phenyl; unsubstituted or substituted aryl; methyl; unsubstituted or substituted $C_2$-$C_6$ straight chain alkyl; unsubstituted or substituted $C_3$-$C_6$ branched alkyl; unsubstituted or substituted $C_3$-$C_8$ cycloalkyl; unsubstituted or substituted $C_3$-$C_6$ alkenyl; unsubstituted or substituted heterocycle; or unsubstituted or substituted heteroaryl. In one embodiment, $R_{10}$ is H and $R_{11}$ is a substituted or unsubstituted phenyl or $C_3$-$C_6$ branched alky. The phenyl can be substituted with halogen, hydroxyl, methyl, —$CF_3$, $C_2$-$C_6$ straight chain alkyl, $C_3$-$C_6$ branched alkyl, $C_3$-$C_8$ cycloalkyl, nitro, cyano, amino, alkylamino, dialkylamino, alkoxy, —$OCF_3$, carboxyacid, carbonylalkyl, carbonylalkoxy, thio, thioalkyl, phenyl, aryl, heterocycle, or heteroaryl. For example, the phenyl is substituted with halogen, hydroxyl, —$CF_3$, nitro, cyano, or alkoxy. In another example, the phenyl is substituted with at least one halogen. For example, the halogen is F. In another example, the branched alkyl is isopropyl.

$R_a$ can also be $R^xR^yR^zSi$—. $R^x$, $R^y$, and $R^z$ can be the same as or different from each other and each represents methyl, ethyl, i-propyl, t-butyl, or phenyl. In one embodiment, $R^x$ and $R^y$ are both phenyl and $R^z$ is t-butyl.

$R_a$ can also be unsubstituted or substituted heterocycle. For example, the heterocycle is pyridine. For example, the pyridine is 3-pyridine.

Compounds of Formula I and II include those in which, $R_3$ is H, unsubstituted or substituted phenyl or unsubstituted or substituted heterocycle. In one embodiment, $R_3$ is unsubstituted phenyl or heterocycle. For example, the heterocycle is piperidine.

Preferred compounds of Formula I and II are those in which, X is alkylamino or dialkylamino, each which may be substituted. The alkylamino or dialkylamino can be —$NR_{12}R_{13}$. $R_{12}$ and $R_{13}$ are each independently H, unsubstituted or substituted $C_1$-$C_6$ straight chain alkyl, $C_3$-$C_6$ branched alkyl, or unsubstituted or substituted benzyl. $R_{12}$ can be substituted with $C_1$-$C_6$ straight chain alkyl. The alkyl can be substituted with acetal. $R_{13}$ can be ethylphenyl or methyl. In one embodiment, $R_{12}$ is H and $R_{13}$ is unsubstituted benzyl or substituted $C_1$-$C_6$ straight chain alkyl.

Compounds of Formula I and II include those in which, $R_5$ and X are both H.

The present invention also provides the compounds of Formula III:

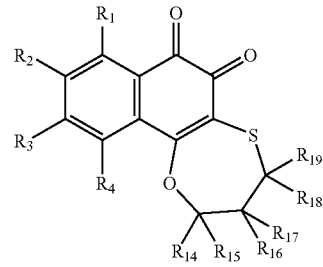

(III)

or a pharmaceutically acceptable salt and/or an individual diastereomer thereof, wherein:

$R_1$, $R_2$, $R_3$, $R_4$, $R_{14}$, $R_{15}$, $R_{16}$, $R_{17}$, $R_{18}$, and $R_{19}$ are each, independently, H, halogen, hydroxyl, unsubstituted or substituted $C_1$-$C_6$ alkyl, unsubstituted or substituted $C_1$-$C_6$ alkenyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, amide, unsubstituted or substituted $C_1$-$C_6$ acyl, $C_1$-$C_6$ alkoxycarbonyl, amino, alkylamino, or dialkylamino.

Compounds of Formula III include those in which $R_6$ is unsubstituted or substituted $C_1$-$C_6$ alkyl. Preferably, $R_6$ is propyl.

Unless defined otherwise, all technical and scientific terms used herein have the same meaning as commonly understood by one of ordinary skill in the art to which this invention belongs. In case of a conflict in terminology, the present specification controls. The following terms generally have the following meanings.

As used herein, the term "alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl). "Alkyl" further includes alkyl groups that have oxygen, nitrogen, or sulfur atoms replacing one or more hydrocarbon backbone carbon atoms. In certain embodiments, a straight chain or branched alkyl has six or fewer carbon atoms in its backbone (e.g., $C_1$-$C_6$ for straight chain, $C_3$-$C_6$ for branched chain), and more preferably four or fewer.

The term "alkyl" also includes both "unsubstituted" and "substituted alkyls", the latter of which refers to alkyl moieties having substituents replacing a hydrogen on one or more carbon of the hydrocarbon backbone. Such substitutents can include, for example, alkyl, alkenyl, alkynyl, hydroxyl, alkylcarbonyl, arylcarbonyl, alkoxycarbonyl, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl ($S(O)_2NH_2$), aminesulfoxide (NHS(O) or S(O)NH), sulfonamide ($NHS(O)_2$ or $S(O)_2NH$), nitro, —$CF_3$, halogen, cyano, azido, heterocyclyl, alkylaryl, or an aromatic or heteroaromatic moiety. An "alkylaryl" or aralkyl moiety is an alkyl moiety substituted with an aryl (e.g., methylphenyl (benzyl)). "Alkyl" also includes the side chains of natural and unnatural amino acids.

Aryl includes groups with aromaticity, including 5- and 6-membered "unconjugated", or single-ring aromatic groups that may include from one to four heteroatoms, as well as "conjugated", or multicyclic systems with at least one aromatic ring. Examples of aryl groups include phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term "aryl" includes multicyclic groups, e.g., tricyclic, bicyclic, e.g., naphthalene, benzoxazole, benzodioxazole, benzothizole, benzoimidazole, benzothiophene, methylenedioxyphenyl, quinoline, isoquinoline, napthridine, indole, benzofuran, purine, benzofuran, deazapureine, or indolizine. Those aryl groups having heteroatoms in the ring structure may also be referred to as "aryl heterocycles", "heterocycles", "heterocyclyls", "heteroaryls" or "heteroaromatics" e.g., pyridine, pyrazole, pyrimidine, furan, isoxazole, imidazole[2,1,b]thiazole, triazole, pyrazine, benzothiophene, imidazole, or thiophene. The aromatic ring can be substituted at one or more ring positions with such substituents as described above, as for example, halogen, hydroxyl, alkyl, alkoxy, alkylcarbonyloxy, arylcarbonyloxy, alkoxycarbonyloxy, aryloxycarbonyloxy, carboxylate, carboxyacid, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, carboxyalkyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, or sulfnur replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, phenyl, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

As used herein, "amine" or "amino" includes compounds where a nitrogen atom is covalently bonded to at least one carbon or heteroatom. "Alkylamino" includes groups of compounds wherein nitrogen is bound to at least one additional alkyl group. Examples of alkylamino groups include benzylamino, methylamino, ethylamino, and phenethylamino. "Dialkylamino" includes groups wherein the nitrogen atom is bound to at least two additional alkyl groups. Examples of dialkylamino groups include dimethylamino and diethylamino. "Arylamino" and "diarylamino" include groups wherein the nitrogen is bound to at least one or two aryl groups, respectively. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl, or heterocycle. Substituents on amide groups may be further substituted.

"Acyl" includes compounds and moieties that contain the acyl radical ($CH_3CO-$) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "cycloalkyl" includes saturated acyclic groups (e.g., cyclopropyl, cyclopentyl, cyclohexyl, cyclohexyl, cycloheptyl, cyclooctyl). Preferred cycloalkyls have from three to eight carbon atoms in their ring structure, and more preferably have five or six carbon atoms in the ring structure. Cycloalkyls includes both "unsubstituted cycloalkyls" and "substituted cycloalkyls", the latter of which refers to replacing a hydrogen on one or more of the carbons in the ring structure. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The terms "heterocyclyl", "heterocycle" or "heterocyclic group" include closed ring structures, e.g., 3, 4, 5, 6, 7, 8, 9, or 10-membered rings, which include one or more heteroatoms. "Heteroatom" includes atoms of any element other than carbon or hydrogen. Examples of heteroatoms include nitrogen, oxygen, or sulfur.

Heterocyclyl groups or heterocycles can be saturated or unsaturated and include pyrrolidine, pyrazine, pyrimidine, oxolane, 1,3-dioxolane, thiolane, tetrahydrofuran, tetrahydropyran, piperidine, piperazine, pyrrolidine, morpholine, lactones, lactams such as azetidinones and pyrrolidinones, sultams, sultones, and protected heterocycles, such as tert-butoxy protected piperazine, in which protecting groups can be removed for further functionalization. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, acetal, alkylcarbonyloxy, arylcarbonyloxy, alkoxycarbonyloxy, aryloxycarbonyloxy, carboxylate, carboxyacid, alkylcarbonyl, alkoxycarbonyl, carbonylalkoxy, aminocarbonyl, alkylthiocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, phenyl, heterocyclyl, aryl or heteroaryl. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like. Substituents on a heterocyclic group can be further substituted e.g., with halogen, amide, hydroxyl, or alkoxy.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "C1-C6" includes one to six carbon atoms (C1, C2, C3, C4, C5 or C6). The term "C2-C6" includes two to six carbon atoms (C2, C3, C4, C5 or C6). The term "C3-C6" includes three to six carbon atoms (C3, C4, C5 or C6). The term "C3-C8" includes two to eight carbon atoms (C3, C4, C5, C6, C7 or C8). The term "C5-C8" includes five to eight carbon atoms (C5, C6, C7 or C8).

It should be noted that any heteroatom or carbon atom with unsatisfied valences is assumed to have the hydrogen atom to satisfy the valences.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

In the specification, the singular forms also include the plural, unless the context clearly dictates otherwise.

A "pharmaceutically acceptable salt" or "salt" of the disclosed compound is a product of the disclosed compound that contains an ionic bond, and is typically produced by reacting the disclosed compound with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The present invention also provides pharmaceutical formulations comprising a compound of Formula I, II or III in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A compound of Formula I, II or III is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of Formula I, II or III (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a compound of Formula I, II or III is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not so high as to cause unacceptable side effects. The state of the disease condition (e.g., cancer, psoriasis, and the like) and the health of the patient should be closely monitored during and for a reasonable period after treatment.

The present invention also provides a method for the treatment of cell proliferative disorders in a mammal comprising administering to a mammal in need of such treatment, an therapeutically effective amount of a compound Formula I, II or III. The invention further provides the use of a compound of Formula I, II or III for the preparation of a medicament useful for the treatment of a cell proliferative disorder. In one embodiment, the invention provides for the treatment of cancer or precancerous conditions in a mammal comprising administering to a mammal in need of such treatment, an therapeutically effective amount of a compound of Formula I, II or III.

An effective amount of a compound of Formula I, II or III is used in a method to treat a cell proliferative disorder in a mammal without affecting normal cells of the mammal. For example, a therapeutically effective amount of a compound of Formula I, II or III is used in a method for treating cancer in a mammal by inducing cell death in cancer cells without affecting normal cells in the mammal. Cell death can occur by either apoptosis or necrosis mechanisms. In another example, administration of a therapeutically effective amount of a compound of Formula I, II or III induces sustained (non-transient) activity (e.g. elevation of the level) of a checkpoint molecule in abnormally proliferating cells without affecting checkpoint molecule activity in normal cells. For example, administration of a therapeutically effective amount of a compound of Formula I, II or III induces activation of E2F1 checkpoint pathway in abnormally proliferating cells without significantly affecting normal cells. In another example, administration induces sustained E2F pathway activity (e.g. elevation of E2F levels) in cancer cells without affecting E2F pathway activity (e.g. E2F levels) in normal cells. Methods of measuring induction of E2F activity and elevation of E2F levels are as shown in Li et al., (2003) *Proc Natl Acad Sci USA.* 100(5): 2674-8. In another embodiment, administration of a therapeutically effective amount of a compound of Formula I, II or III induces cell death in abnormally proliferating cells without inducing cell death in normal cells.

The invention also provides a method of protecting against a cell proliferative disorder in a mammal by administering a therapeutically effective amount of a compound of Formula I, II or III to a mammal. The invention also provides the use of a compound of Formula I, II or III for the preparation of a medicament useful for the prevention of a cell proliferative disorder. In one embodiment, the invention provides for the prevention of cancer in a mammal comprising administering to a mammal in need of such treatment, a therapeutically effective amount of a compound of Formula I, II or III.

The compounds of the invention are administered in the form of pharmaceutical compositions, e.g., as described herein.

The mammal can be e.g., any mammal, e.g., a human, a primate, mouse, rat, dog, cat, cow, horse, pig. For example, the mammal is a human.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

The invention also provides methods for the synthesis of the compounds of Formula I, II, III. In one embodiment, the present invention provides a method for the synthesis of compounds according to scheme 1-2 and protocols A-B.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Schemes 1-2 and protocols A-B depicts a general synthesis for a family of compounds of the invention. Compounds encompassed in the invention can be produced according to this or other synthetic processes without departing from the spirit or essential characteristics of the invention. All changes that come within the meaning and range of equivalency of the compounds are intended to be embraced herein. Thus, it is expected that one of ordinary skill in the art would know how to alter the synthetic schemes illustrated herein so as to produce a desired substitution pattern on a compound, produce an increased or decreased product yield, minimize reaction side products, eliminate the use of dangerous or toxic chemical reactants, and/or to produce a desired amount of product (e.g., scale-up reaction size for commercial manufacture), and the like.

The invention will be further described in the following examples, which do not limit the scope of the invention described in the claims.

EXAMPLES

General

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$.; John Wiley & Sons: New York, 1999, incorporated by reference herein, are useful and recognized reference textbooks of organic synthesis known to those in the art. The following descriptions of synthetic methods are designed to illustrate, but not limit, general procedures for the preparation of compounds of the invention.

The compounds of this invention with general formula (I) may be prepared according to the following schemes from commercially available starting materials or starting materials, which can be prepared using literature procedures. These schemes show the preparation of representative compounds of this invention.

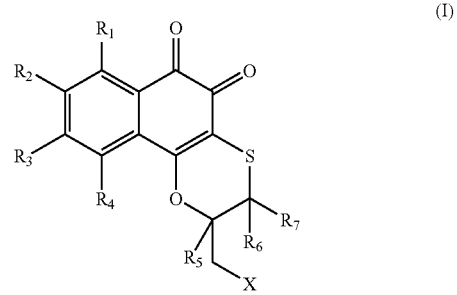

(I)

The compounds of the present invention can be prepared from the reaction of 1,2-quinone alcohol (II) and appropriate intermediate/commercial reagents as shown in Scheme 1.

Scheme 1

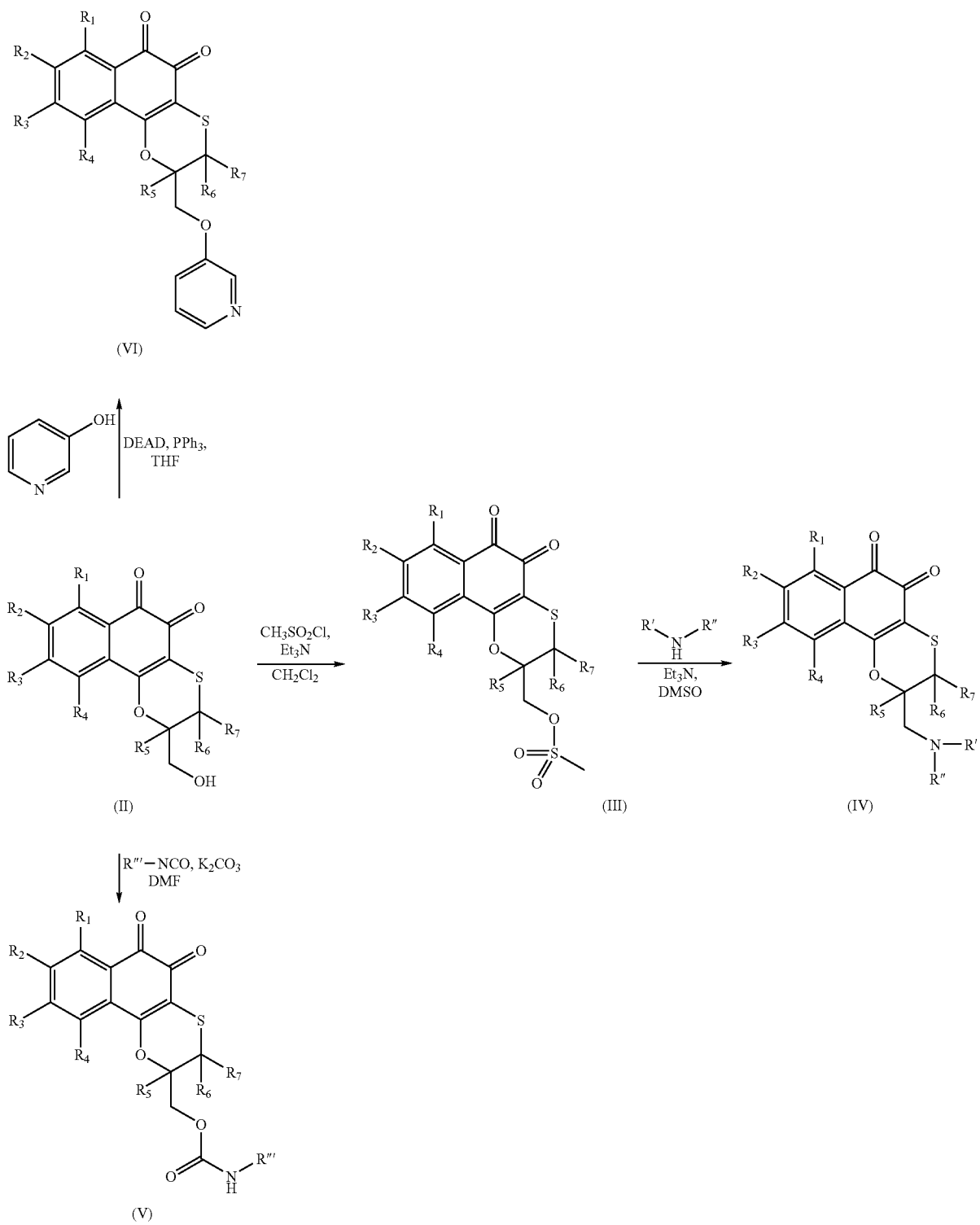

Compounds of formula (IV) where R' and R" are substituents on either primary or secondary amines reagents, can be conveniently prepared by a variety of methods familiar to those skilled in the art. One common route is illustrated in Scheme 1. 1,2-Quinone mesylate (III) can be conveniently prepared by treating 1,2-quinone alcohol (II) with methanesulfonyl chloride, tertiary amine bases such as triethyl amine, diisopropylethyl amine in solvents such as dichloromethane for 0.5-4 hours at 0° C. to ambient temperatures. The 1,2-quinone mesylate (III) is treated with primary and secondary amines, tertiary amine bases such as triethyl amine, diisoproylethyl amine, dimethylamino pyridine in solvents such as dimethylsulfoxide for 0.5-4 hours at ambient temperatures to 80° C. to provide 1,2-quinone amines (IV). Many primary and secondary amines are commercially available or readily prepared by methods described in the literature and known to those skilled in art.

quinone alcohol (II) with pyridine-3-ol, under mitsunobu conditions using triphenyl phosphine, DEAD (diethylazidodicarboxylate) in solvents such as THF (tetrahydrofuran) for 6-24 hours at ambient temperatures. Alternatively activating reagents such as DIAD, DBAD can also be used.

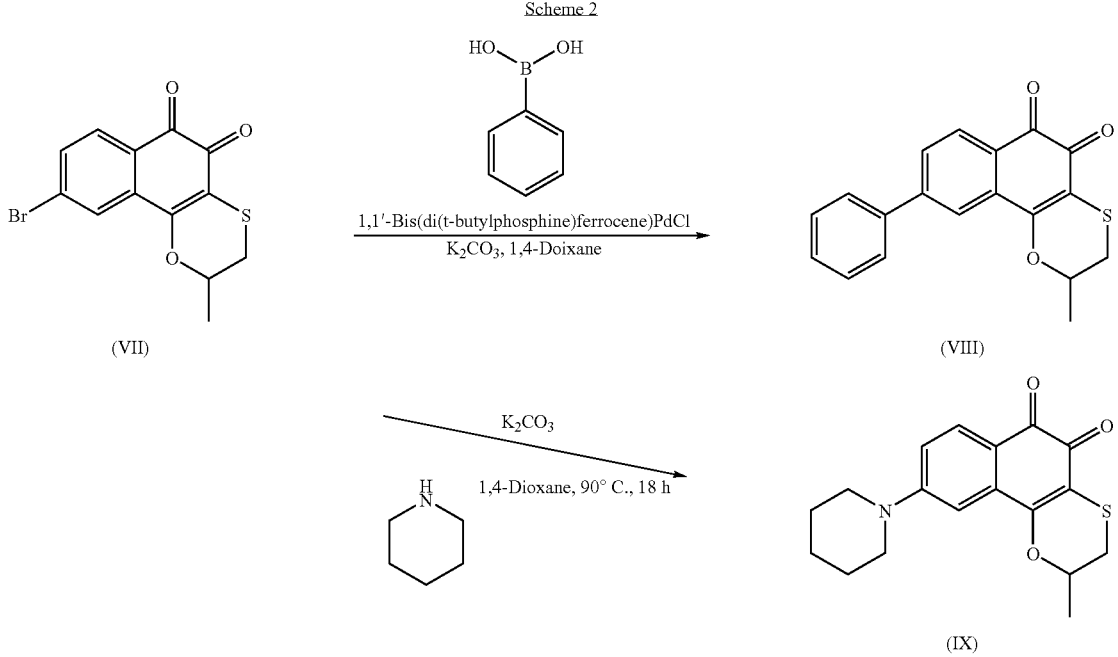

The 1,2-quinone amines (IV) formed from the reaction of primary amines with the 1,2-quinone mesylate (III) could be further functionalized with acid chlorides and carboxylic acids to form amides, sulfonyl chlorides to form sulfonamides, isocyanates to form ureas, carbamoyl chlorides to form carbamates, sulfonyl isocyanates to form sulfonyl ureas, epoxides to form amino alcohols, heterocyclic halides to form amino heterocycles, anhydrides to form keto alkyl or aryl acids, alkyl or aryl bromides, iodides to form amino alkyls or amino aryls. The methods to carry out the above transformations are described in reference text's such as Comprehensive Organic Transformations, Richard C. Larock, Second Edition, Wiley-VCH, 1999; Protective Groups in Organic Synthesis, Third Edition, Theodora W. Greene and Peter M. Wuts, Wiley Interscience, 1999; The Practice of Peptide Synthesis, M. Bodanszky and A. Bodanzsky, Springer-Verlag, 1984.

Compounds of formula (V) where R''' are alkyl or aryl can be conveniently prepared by a variety of methods familiar to those skilled in the art. One common route is illustrated in Scheme 1. 1,2-Quinone carbamates (V) can be conveniently prepared by treating 1,2-quinone alcohol (II) with alkyl or aryl isocyanates, bases such as potassium carbonate in solvents such as DMF (dimethylformamide) for 1-4 hours at ambient temperatures to 60° C. Alternatively bases such as sodium carbonate, sodium bicarbonate, triethyl amine, diisoproylethyl amine can also be used. Many isocyanates are commercially available or readily prepared by methods described in the literature and known to those skilled in art.

Compounds of formula (VI) can be conveniently prepared by a variety of methods familiar to those skilled in the art. One common route is illustrated in Scheme 1. 1,2-Quinone aryl ethers (VI) can be conveniently prepared by treating 1,2-

The compounds of the present invention can be prepared from the reaction of 1,2-quinone (VII) and appropriate intermediate/commercial reagents as shown in Scheme 2. Compounds of formula (VIII) can be conveniently prepared by a variety of methods familiar to those skilled in the art. One common route is illustrated in Scheme 2. Bromo-1,2-quinone (VII) is treated with a palladium catalyst such as 1,1'-bis{di(t-butylphosphine)ferrocene}PdCl, boronic acids such as phenyl boronic acid, bases such as potassium carbonate in solvents such as 1,4-dioxane for 2-8 hours at 60-100° C. to provide phenyl substituted 1,2-quinone (VIII). Alternatively bases such as sodium carbonate, cesium carbonate can also be used. Many aromatic boronic acids are commercially available or readily prepared by methods described in the literature and known to those skilled in art. (Prieto M. et al, JOC, 2004, 69(20), 6812)

Compounds of formula (IX) can be conveniently prepared by a variety of methods familiar to those skilled in the art. One common route is illustrated in Scheme 2. Bromo-1,2-quinone (VII) is treated with amines such as piperidine, bases such as potassium carbonate in solvents such as 1,4-dioxane for 12-24 hours at 60-110° C. to provide amine substituted 1,2-quinone (VIII). Alternatively bases such as sodium carbonate, cesium carbonate and palladium(0) catalysts such as bis(tri-tert-butyl phosphine)palladium(0) can also be used. (J. Am. Chem. Soc., 2002, 124, 14844) Many secondary amines are commercially available or readily prepared by methods described in the literature and known to those skilled in art.

Scheme 3

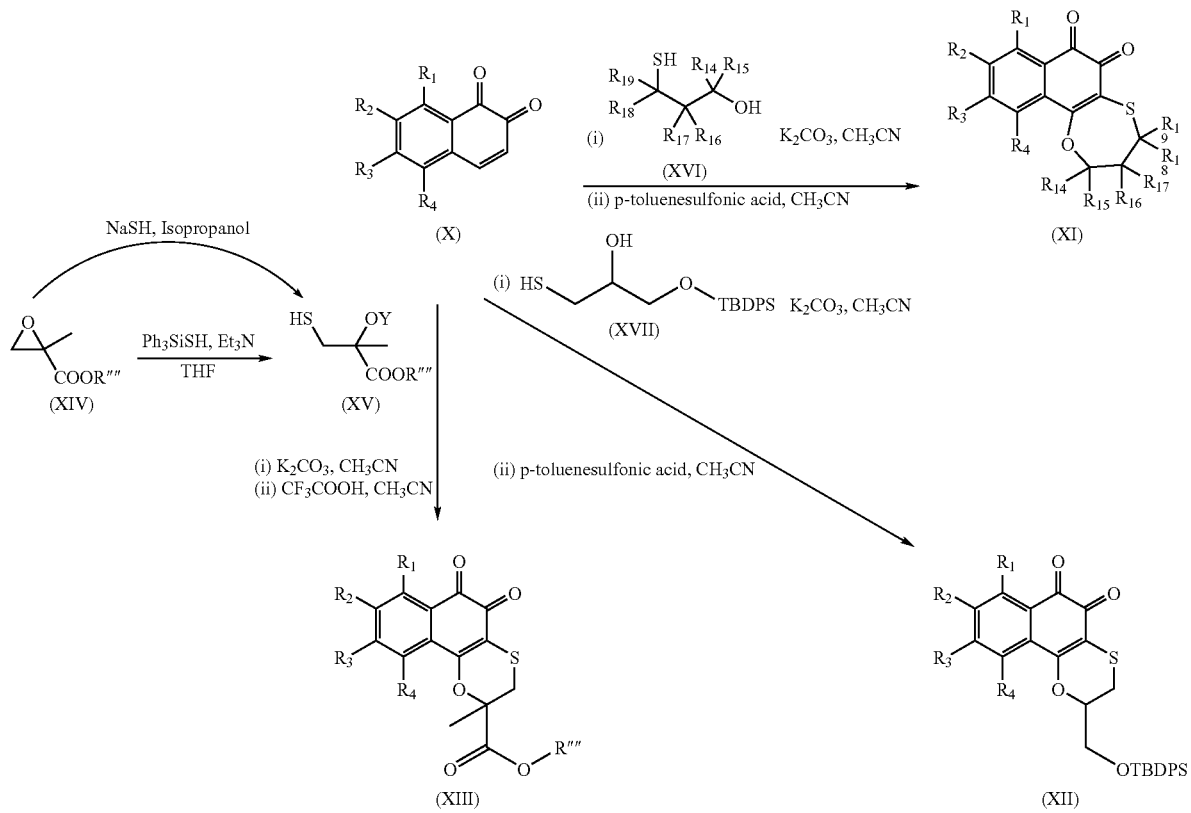

Compounds of formula (XI-XIII) can be conveniently prepared starting with 1,2-quinone (X) by a variety of methods familiar to those skilled in the art. One common route is illustrated in Scheme 3.

1,2-Quinones oxathiine (XI) can be conveniently prepared in two steps. Step (i) 1,2-quinone (X) is treated with propane-1,3-thioalcohols (XVI), bases such as potassium carbonate in solvents such as acetonitrile for 0.5-4 hours at ambient temperatures. Step (ii) the crude product from step (i) is treated with acids such as p-toluenesulfonic acid in solvents such as acetonitrile for 4-24 hours at ambient temperatures to provide 1,2-quinones oxathiine (XI). Alternatively bases such as triethyl amine, diisopropylethyl amine, cesium carbonate, sodium carbonate, sodium bicarbonate and solvents such as dichloromethane, tetrahydrofuran can also be used in step (i). Acid such as trifluoroacetic acid in solvents such as dichloromethane can also be used in step (ii). Many propane-1,3-thioalcohols (XVI) are commercially available or readily prepared by methods described in the literature and known to those skilled in art.

1,2-Quinones oxathiine (XII) can be conveniently prepared in two steps. Step (i) 1,2-quinone (X) is treated with protected 1,2-thioalcohol (XVII), bases such as potassium carbonate in solvents such as acetonitrile for 0.5-4 hours at ambient temperatures. Step (ii) the crude product from step (i) is treated with acids such as p-toluenesulfonic acid in solvents such as acetonitrile for 4-24 hours at ambient temperatures to provide 1,2-quinones oxathiine (XII). Alternatively bases such as triethyl amine, diisopropylethyl amine, cesium carbonate, sodium carbonate, sodium bicarbonate and solvents such as dichloromethane, tetrahydrofuran can also be used in step (i). Acid such as trifluoroacetic acid in solvents such as dichloromethane can also be used in step (ii). Many 1,2-thioalcohols are commercially available or readily prepared by methods described in the literature and known to those skilled in art.

1,2-Quinones oxathiine (XIII) where R'''' is methyl or isopropyl group can be conveniently prepared in two steps using the 1,2-thioalcohols (XV). The thioalcohols (XV) where Y is a triphenylsilane protecting group and R'''' is methyl or isopropyl can be prepared by treating epoxides (XIV) with triphenylsilanethiol, tertiary amine bases such as triethylamine, diisopropylethyl amine in solvents such as tetrahydrofuran for 1-5 hours at ambient temperatures. Alternatively, thioalcohols (XV) where Y is hydrogen can be prepared by treating epoxides (XIV) with thiol sources such as sodium hydrosulfide, sodium sulfide in solvents such as isopropanol for 1-5 hours at ambient temperatures. The 1,2-thioalcohols (XV) are treated with 1,2-quinone (X) to prepare 1,2-quinones oxathiine (XIII) in a two-step procedure. Step (i) 1,2-quinone (X) is treated with 1,2-thioalcohol (XV), bases such as potassium carbonate in solvents such as acetonitrile for 0.5-4 hours at ambient temperatures. Step (ii) the crude product from step (i) is treated with acids such as p-toluenesulfonic acid in solvents such as acetonitrile for 4-24 hours at ambient temperatures to provide 1,2-quinones oxathiine (XIII). Alternatively bases such as triethyl amine, diisopropylethyl amine, cesium carbonate, sodium carbonate, sodium bicarbonate and solvents such as dichloromethane, tetrahydrofuran can also be used in step (i). Acids such as trifluoroacetic acid in solvents such as dichloromethane can also be used in step (ii). Many epoxides are commercially available or readily prepared by methods described in the literature and known to those skilled in art.

Example 1

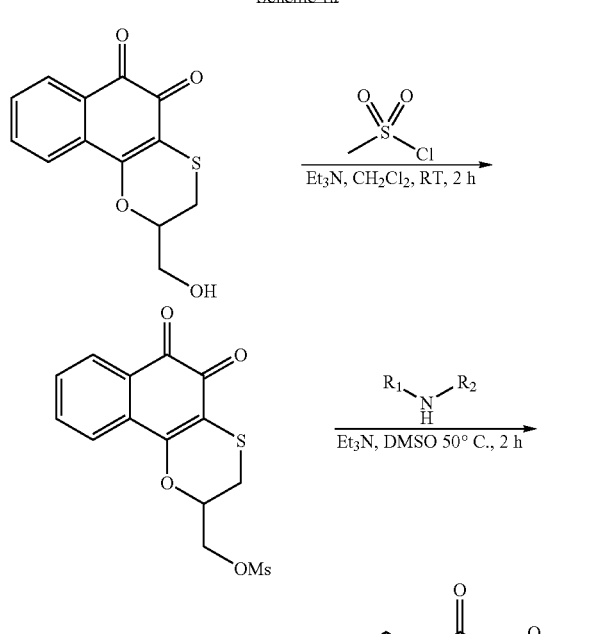

Synthesis of (5,6-dioxo-2,3,5,6-tetrahydronaphtho[1,2-b][1,4]oxathiin-2-yl)methyl methanesulfonate

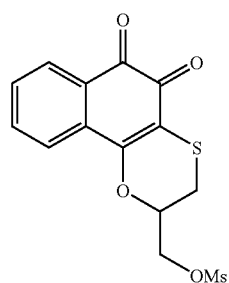

To a solution of 2-(hydroxymethyl)-2,3-dihydronaphtho[1,2-b][1,4]oxathiine-5,6-dione (1.0 g, 3.81 mmol) in dichloromethane (10 mL) was added triethylamine (1.0 mL, 7.63 mmol) and methanesulfonyl chloride (0.60 mL, 7.63 mmol). The resulting mixture was stirred for 1.5 hours at room temperature. Product was collected by filtration, washed with dichloromethane (10 mL) and dried under reduced pressure to provide the product as a purple solid (1.1 g, 85%). M.p.=230-232° C.; 400 MHz $^1$H NMR (DMSO-$d_6$) δ: 7.89 (d, J=6.8 Hz, 1H), 7.75 (m, 2H), 7.56 (m, 1H), 4.81 (m, 1H), 4.65 (m, 1H), 4.54 (m, 1H), 3.05 (m, 2H), 1.16 (m, 3H); LCMS: 341 [M+H].

Example 2

Procedure A

Synthesis of ethyl 4-[(5,6-dioxo-2,3,5,6-tetrahydronaphtho[1,2-b][1,4]oxathiin-2-yl)methyl]piperazine-1-carboxylate (Compound 1)

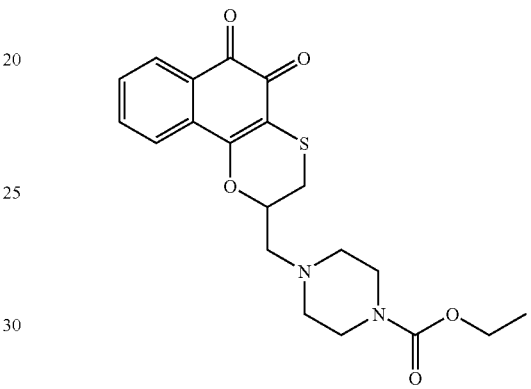

To a solution of (5,6-dioxo-2,3,5,6-tetrahydronaphtho[1,2-b][1,4]oxathiin-2-yl)methyl methanesulfonate (0.15 g, 0.44 mmol) in DMSO (1.5 mL) was added ethyl piperazine-1-carboxylate (0.065 mL, 0.88 mmol) and triethylamine (0.12 mL, 0.88 mmol). The reaction mixture was shaken at 50° C. for 2 hours. The crude product was purified by reverse phase HPLC to give the desired product as a purple solid (0.015 g, 5%). M.p.=185-187° C.; 300 MHz $^1$H NMR (CDCl$_3$) δ: 8.04 (d, J=7.2 Hz, 1H), 7.66 (m, 2H), 7.48 (t, J=7.2 Hz, 1H), 4.66 (m, 1H), 4.15 (m, 2H), 3.51 (m, 4H), 3.23 (m, 1H), 3.03 (m, 1H), 2.83 (m, 2H), 2.54 (m, 4H), 1.27 (m, 3H); LCMS: 403 [M+H].

Synthesis of 2-{[4-(hydroxymethyl)piperidin-1-yl]methyl}-2,3-dihydronaphtho[1,2-b][1,4]oxathiine-5,6-dione (Compound 2)

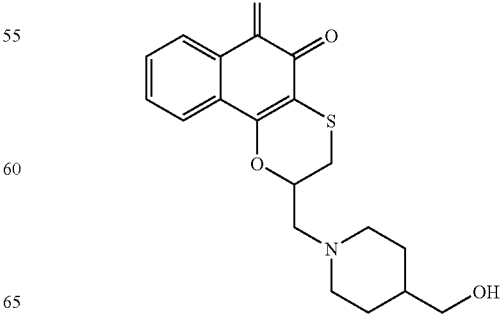

Compound 2 was synthesized using piperidin-4-ylmethanol and conditions outlined in general procedure A. (0.020 g, 13%). M.p.=200-202° C.; 300 MHz $^1$H NMR (CDCl$_3$) δ: 8.04 (d, J=7.5 Hz, 1H), 7.67 (m, 2H), 7.48 (t, J=7.8 Hz, 1H), 5.31 (s, 1H), 4.64 (m, 1H), 3.51 (d, J=6.3 Hz, 2H), 3.23 (d, J=14.1 Hz, 1H), 3.0 (m, 2H), 2.85 (m, 2H), 2.19 (m, 2H), 1.75 (m, 2H), 1.52 (m, 2H), 1.29 (m, 2H); LCMS: 360 [M+H].

Synthesis of 2-[(4-hydroxypiperidin-1-yl)methyl]-2,3-dihydronaphtho[1,2-b][1,4]oxathiine-5,6-dione (Compound 3)

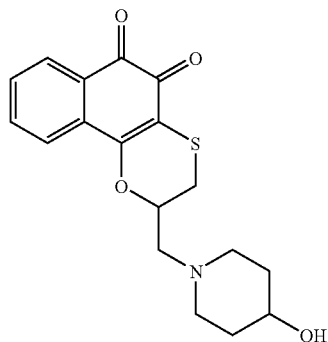

Compound 3 was synthesized using piperidin-4-ol and conditions outlined in general procedure A. (0.018 g, 12%). M.p.=98-100° C.; 300 MHz $^1$H NMR (CDCl$_3$) δ: 8.04 (d, J=7.2 Hz, 1H), 7.66 (m, 2H), 7.48 (t, J=7.8 Hz, 1H), 5.30 (s, 1H), 4.64 (m, 1H), 3.75 (m, 1H), 3.23 (d, J=13.2 Hz, 1H), 2.98 (m, 1H), 2.83 (m, 2H), 2.38 (m, 2H), 1.91 (m, 2H), 1.61 (m, 4H); LCMS: 346 [M+H].

Synthesis of 2-{[(2,2-dimethoxyethyl)(methyl)amino]methyl}-2,3-dihydronaphtho[1,2-b][1,4]oxathiine-5,6-dione (Compound 4)

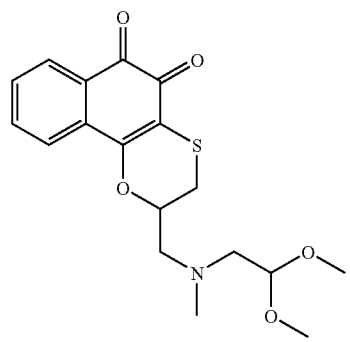

Compound 4 was synthesized using (2,2-dimethoxyethyl)methylamine and conditions outlined in general procedure A (0.021 g, 13%). M.p.=80-82° C.; 400 MHz $^1$H NMR (CDCl$_3$) δ: 8.04 (d, J=8.0 Hz, 1H), 7.72 (d, J=7.6 Hz, 1H), 7.62 (t, J=7.6 Hz, 1H), 7.46 (t, J=7.6 Hz, 1H), 4.63 (m, 1H), 4.47 (m, 1H), 3.41 (m, 1H), 3.36 (s, 3H), 3.35 (s, 3H), 3.23 (d, J=13.6 Hz, 1H), 3.03-286 (m, 4H), 2.67 (m, 2H), 2.46 (s, 3H); LCMS: 364 [M+H].

Synthesis of -{[4-(4-fluorophenyl)piperazin-1-yl]methyl}-2,3-dihydronaphtho[1,2-b][1,4]oxathiine-5,6-dione (Compound 5)

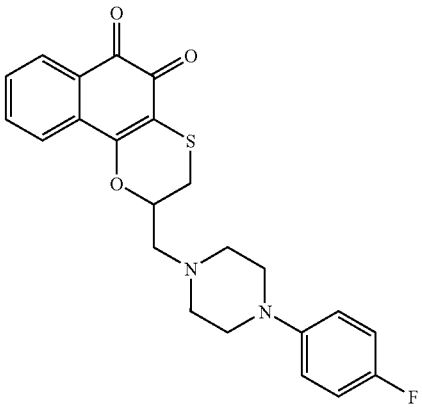

Compound 5 was synthesized using 1-(4-fluorophenyl)piperazine and conditions outlined in general procedure A (0.026 g, 14%). M.p.=180-182° C.; 300 MHz $^1$H NMR (CDCl$_3$) δ: 8.05 (d, J=7.5 Hz, 1H), 7.73 (d, J=7.2, 1H), 7.64 (t, J=7.2 Hz, 1H), 7.48 (t, J=7.5, 1H), 6.96 (m, 2H), 6.89 (m, 2H), 4.69 (m, 1H), 3.26 (d, J=13.8 Hz, 1H), 3.15 (m, 4H), 3.05 (m, 1H), 2.92 (m, 2H), 2.77 (m, 4H); LCMS: 425 [M+H].

Synthesis of 2-{[(2-phenylethyl)amino]methyl}-2,3-dihydronaphtho[1,2-b][1,4]oxathiine-5,6-dione (Compound 6)

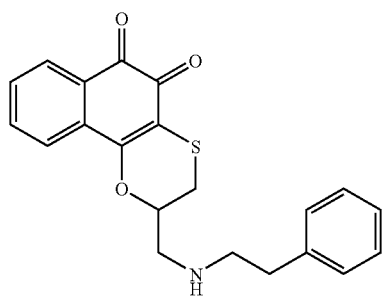

Compound 6 was synthesized using (2-phenylethyl)amine and conditions outlined in general procedure A (0.027 g, 17%). M.p.=80-82° C.; 400 MHz $^1$H NMR (CDCl$_3$) δ: 8.01 (m, 1H), 7.41 (m, 2H), 7.30 (t, J=6.0, 1H), 7.24 (m, 2H), 7.14 (m, 2H), 6.91 (m, 1H), 4.57 (m, 1H), 3.87 (m, 1H), 3.50 (m, 1H), 3.08 (m, 2H), 2.83 (m, 2H), 2.59 (m, 2H); LCMS: 366 [M+H].

Synthesis of 2-[(benzylamino)methyl]-2,3-dihydronaphtho[1,2-b][1,4]oxathiine-5,6-dione (Compound 7)

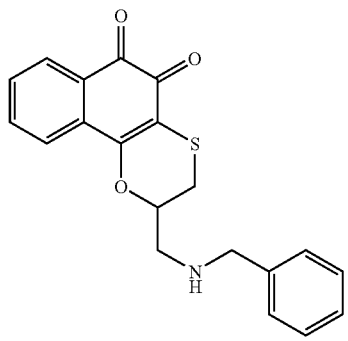

Compound 7 was synthesized using benzylamine and conditions outlined in general procedure A (0.018 g, 12%). M.p.=60-62° C.; 400 MHz $^1$H NMR (CDCl$_3$) δ: 8.01 (d, J=5.7, 1H), 7.65 (m, 2H), 7.42 (m, 1H), 7.19 (m, 3H), 7.11 (m, 2H), 4.61 (m, 1H), 3.69 (m, 1H), 3.52 (m, 1H), 3.18 (m, 2H), 2.53 (m, 2H); LCMS: 352 [M+H].

Synthesis of 2-{4-[(5,6-dioxo-2,3,5,6-tetrahydronaphtho[1,2-b][1,4]oxathiin-2-yl)methyl]piperazin-1-yl}-N-isopropylacetamide (Compound 8)

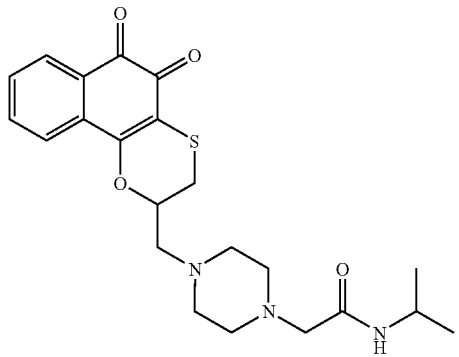

Compound 8 was synthesized using N-isopropyl-2-piperazin-1-ylacetamide and conditions outlined in general procedure A (0.022 g, 12%). M.p.=85-87° C.; 300 MHz $^1$H NMR (CDCl$_3$) δ: 8.04 (d, J=7.2 Hz, 1H), 7.67 (m, 2H), 7.48 (t, J=7.5 Hz, 1H), 6.89 (bd, J=7.2 Hz, 1H), 4.66 (m, 1H), 4.11 (m, 1H), 3.22 (d, J=13.2, 1H), 3.03 (m, 1H), 2.99 (s, 2H), 2.83 (m, 2H), 2.64 (m, 8H), 1.17 (m, 6H); LCMS: 430 [M+H].

Synthesis of 2-(1,4-dioxa-8-azaspiro[4.5]dec-8-ylmethyl)-2,3-dihydronaphtho[1,2-b][1,4]oxathiine-5,6-dione (Compound 9)

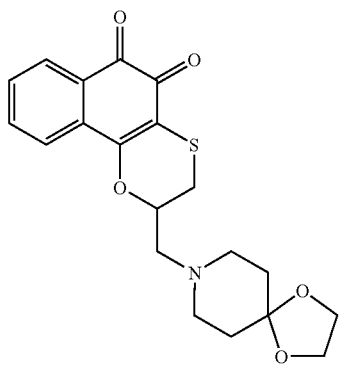

Compound 9 was synthesized using 1,4-dioxa-8-azaspiro[4.5]decane and conditions outlined in general procedure A (0.022 g, 13%). M.p.=202-204° C.; 300 MHz $^1$H NMR (CDCl$_3$) δ: 8.04 (d, J=7.5 Hz, 1H), 7.66 (m, 2H), 7.47 (t, J=7.5 Hz, 1H), 3.96 (m, 1H), 4.11 (m, 4H), 3.23 (d, J=13.2, 1H), 3.01 (m, 1H), 2.83 (m, 2H), 2.69 (m, 4H), 1.77 (t, J=5.7, 4H); LCMS: 388 [M+H].

Example 3

Scheme II

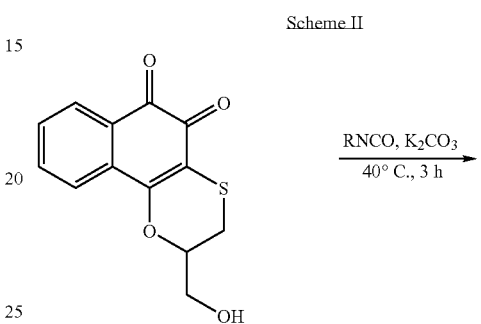

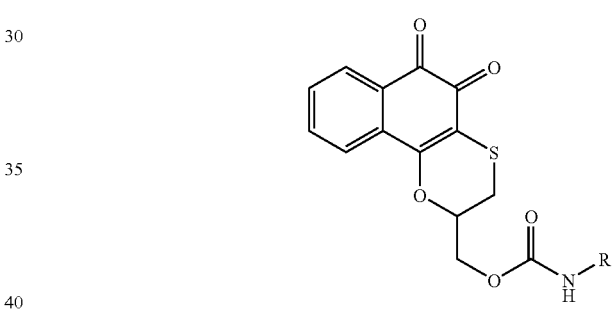

Example 4

Procedure B

Synthesis of (5,6-dioxo-2,3,5,6-tetrahydronaphtho[1,2-b][1,4]oxathiin-2-yl)methyl (4-fluorophenyl)carbamate (Compound 10)

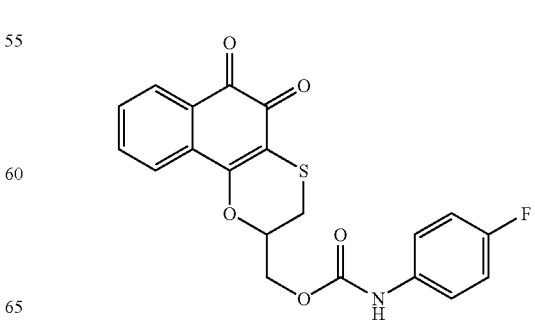

To a solution of 2-(hydroxymethyl)-2,3-dihydronaphtho[1,2-b][1,4]oxathiine-5,6-dione (0.13 g, 0.50 mmol) in N,N-dimethylformamide (1.5 mL) was added 1-fluoro-4-isocyanatobenzene (0.024 mL, 0.55 mmol) and potassium carbonate (0.026 g, 0.50 mmol). The mixture was stirred at 40° C. for 3 hours. The reaction mixture was filtered and the filtrate concentrated under reduced pressure. The crude mixture was purified by flash column chromatography (SiO$_2$, 10% methanol in EtOAc) to give the product as a purple solid (0.051 g, 26%). M.p.=235-237° C.; 300 MHz $^1$H NMR (DMSO-d$_6$) δ: 9.89 (s, 1H), 7.89 (d, J=7.5, 1H), 7.71 (br. s, 2H), 7.50 (m, 3H), 7.12 (m, 2H), 4.78 (m, 1H), 4.53 (m, 2H), 3.18 (m, 2H); LCMS: 400 [M+H].

Synthesis of (5,6-dioxo-2,3,5,6-tetrahydronaphtho[1,2-b][1,4]oxathiin-2-yl)methyl phenylcarbamate (Compound 11)

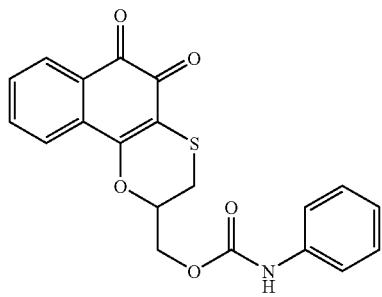

Compound 11 was synthesized using isocyanatobenzene and conditions outlined in general procedure B. (0.046 g, 24%). M.p.=250-252° C.; 400 MHz $^1$H NMR (DMSO-d$_6$) δ: 9.83 (s, 1H), 7.87 (d, J=7.6, 1H), 7.72 (m, 2H), 7.51 (m, 1H), 7.45 (d, J=8, 2H), 7.27 (m, 2H), 6.98 (m, 1H), 4.77 (m, 1H), 4.52 (m, 2H), 3.16 (m, 2H); LCMS: 382 [M+H].

Synthesis of (5,6-dioxo-2,3,5,6-tetrahydronaphtho[1,2-b][1,4]oxathiin-2-yl)methyl isopropylcarbamate (Compound 12)

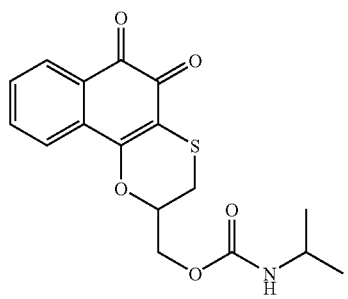

Compound 12 was synthesized using 2-isocyanatopropane and conditions outlined in general procedure B. (0.055 g, 32%). M.p.=218-220° C.; 300 MHz $^1$H NMR (CDCl$_3$) δ: 8.04 (d, J=7.5, 1H), 7.74 (d, J=7.5, 1H), 7.64 (t, J=7.5, 1H), 7.48 (m, 1H), 4.67 (br. s, 1H), 4.48 (m, 2H), 3.84 (br. m, 1H), 3.10 (m, 2H), 1.18 (d, J=6.0, 6H); LCMS: 348 [M+H].

Synthesis of 4-propyl-3,4-dihydro-2H-naphtho[1,2-b][1,4]oxathiepine-6,7-dione (Compound 13)

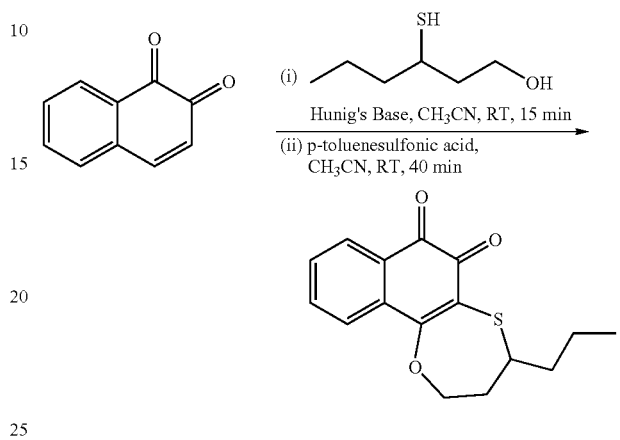

To a solution of naphthalene-1,2-dione (1.5 g, 9.5 mmol) in acetonitrile (50 mL) was added 3-mercaptohexan-1-ol (1.6 g, 11.9 mmol) followed by the addition of diisopropylethylamine (1.65 mL, 9.5 mmol). The mixture was stirred at room temperature for 30 minutes. The solvent was removed under reduced pressure and the residue dissolved in ethyl acetate (50 mL). The organic layer was washed with water (30 mL), dried with sodium sulfate and concentrated under reduced pressure. The resulting residue was dissolved in acetonitrile (35 mL) and reacted with p-toluenesulfonic acid (1.9 g). The reaction mixture was stirred at room temperature for 40 min and solvent removed under reduced pressure. Crude product was purified by flash column (5% EtOAc in hexane to 15% EtOAc in hexanes) to give product as purple solid (0.170 g). M.p.=74-75° C. (decomposition); 400 MHz $^1$H NMR (DMSO-d$_6$) δ: 7.88 (d, J=7.2 Hz, 1H), 7.73 (m, 2H), 7.56 (m, 1H), 5.08 (m, 1H), 4.67 (m, 1H), 3.58 (m, 1H), 1.40-1.82 (m, 6H), 0.89 (brt, 3H); LCMS: 289 [M+H].

Synthesis of 2-methyl-9-phenyl-2,3-dihydronaphtho[1,2-b][1,4]oxathiine-5,6-dione (Compound 14)

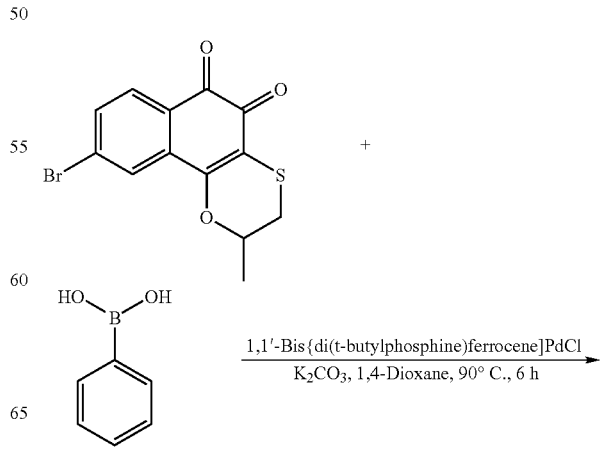

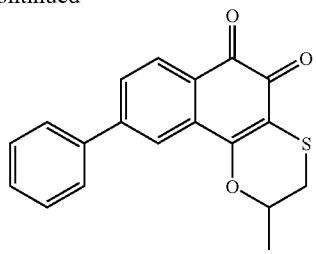

To a solution of 9-bromo-2-methyl-2,3-dihydronaphtho[1,2-b][1,4]oxathiine-5,6-dione (0.1 g, 0.31 mmol) in 1,4-dioxane (1.0 mL) was added phenylboronic acid (0.056 g, 0.459 mmol), potassium carbonate (0.118 g, 0.857 mmol) and 1,1'-bis[di(t-butylphosphine)ferrocene]PdCl (0.02 g, 0.031 mmol). The reaction mixture was heated at 90° C. for 6 hours. The resulting mixture was filtered and solvent removed under reduced pressure. The crude mixture was purified by flash column chromatography (SiO$_2$, 16% EtOAc in hexanes) to give the product as a purple solid (0.024 g, 20%). M.p.=190-192° C.; 400 MHz $^1$H NMR (CDCl$_3$) δ: 8.11 (d, J=7.6, 1H), 7.93 (d, J=1.6, 1H), 7.66 (m, 3H), 7.45 (m, 3H), 4.70 (m, 1H), 3.11 (d, J=13.2, 1H), 2.94 (m, 1H), 1.65 (m, 3H); LCMS: 323 [M+H].

Synthesis of 2-methyl-9-piperidin-1-yl-2,3-dihydronaphtho[1,2-b][1,4]oxathiine-5,6-dione (Compound 15)

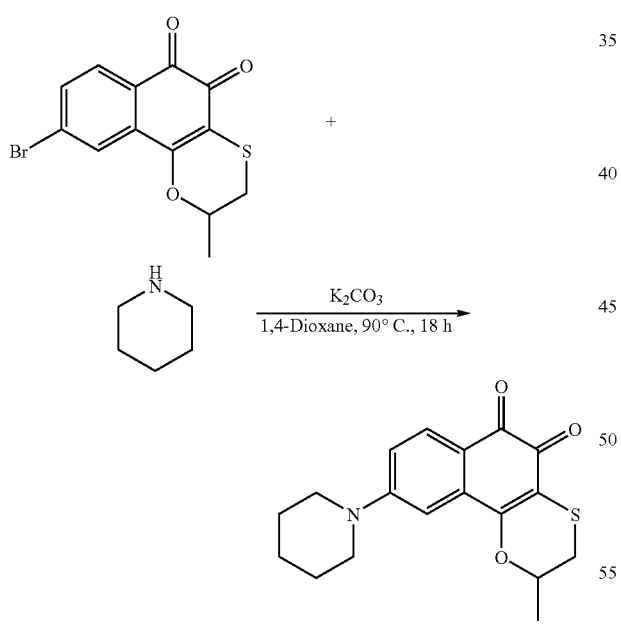

To a solution of 9-bromo-2-methyl-2,3-dihydronaphtho[1,2-b][1,4]oxathiine-5,6-dione (0.1 g, 0.31 mmol) in 1,4-dioxane (1.0 mL) was added piperidine (0.061 mL, 0.616 mmol) and potassium carbonate (0.043 g, 0.308 mmol). The reaction mixture was stirred at 90° C. for 18 hours. The resulting mixture was filtered and solvent was removed under reduced pressure. The crude mixture was purified by flash column chromatography (SiO$_2$, 50% EtOAc in hexanes) to give the product as a purple solid (0.025 g, 25%). M.p.=225-226° C.; 400 MHz $^1$H NMR (CDCl$_3$) δ: 7.91 (d, J=8.8, 1H), 7.09 (d, J=2.8, 1H), 6.72 (m, 1H), 4.62 (m, 1H), 3.49 (m, 4H), 3.07 (d, J=13.6, 1H), 2.88 (m, 1H), 1.71 (br. s, 6H), 1.60 (d, J=6.4, 3H); LCMS: 330 [M+H].

Synthesis of 2-({[tert-butyl(diphenyl)silyl]oxy}methyl)-2,3-dihydronaphtho[1,2-b][1,4]oxathiine-5,6-dione (Compound 16)

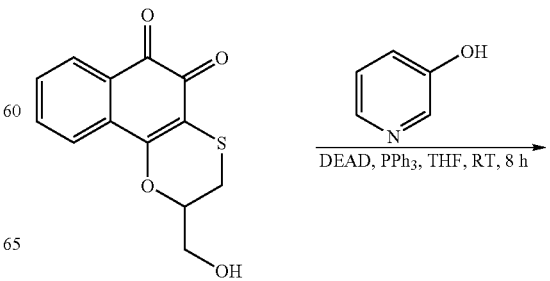

To a solution of naphthalene-1,2-dione (0.103 g, 0.65 mmol) in acetonitrile (4.0 mL) was added 1-{[tert-butyl(diphenyl)silyl]oxy}-3-mercaptopropan-2-ol (0.226 g, 0.065 mmol) followed by diisopropylethylamine (0.114 mL, 0.065 mmol). The reaction mixture was stirred for 10 minutes at room temperature followed by addition of ethyl acetate (10 mL). The organic layer was washed with water (10 mL) and 1.0 N HCl (5 mL). The organic layer was dried with sodium sulfate and concentrated under reduced pressure. (ii) To the residue was added p-toluenesulfonic acid (0.48 g, mmol) followed by acetonitrile (5 mL). The reaction mixture was stirred at room temperature for 2 hours. To the reaction mixture was added ethyl acetate (10 mL) and the organic layer was extracted with water (10 mL). The organic layer was dried with sodium sulfate and concentrated under reduced pressure. The crude mixture was purified by flash column chromatography (SiO$_2$, 100% dichloromethane) to give the product as a purple solid (0.061 g, 18%). M.p.=205-210° C.; 400 MHz $^1$H NMR (CDCl$_3$) δ: 8.4-8.1 (m, 1H), 7.75-7.5 (m, 6H), 7.49-7.3 (m, 7H), 4.65-4.58 (m, 1H), 4.1-3.93 (m, 2H), 3.2-3.05 (m, 2H), 1.08 (s, 9H); LCMS: 501 [M+H].

Synthesis of 2-[(pyridin-3-yloxy)methyl]-2,3-dihydronaphtho[1,2-b][1,4]oxathiine-5,6-dione (Compound 17)

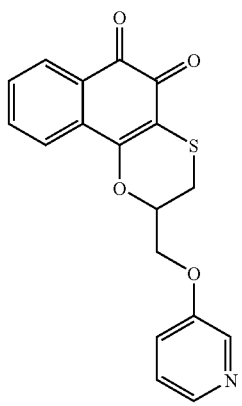

To a solution of 2-(hydroxymethyl)-2,3-dihydronaphtho[1,2-b][1,4]oxathiine-5,6-dione (0.35 g, 1.34 mmol) in tetrahydrofuran (10.0 mL) was added triphenylphosphine (1.4 g, 5.34 mmol) and pyridin-3-ol (0.507 g, 5.34 mmol) followed by diethyl (Z)-diazene-1,2-dicarboxylate (0.53 mL, 3.34 mmol). The reaction mixture was stirred at room temperature for 8 hours. The reaction was quenched by addition of water (30 mL). The aqueous layer was extracted with dichloromethane (2×20 mL). The organic extracts were combined and extracted thrice with 1.0N HCl (10 mL). The HCl extracts were combined and its pH adjusted to 9 with a saturated sodium carbonate solution. The aqueous layer was extracted with dichloromethane (2×20 mL), extracts combined, dried with sodium sulfate and concentrated under reduced pressure. The crude mixture was purified by flash column chromatography (SiO$_2$, 50% EtOAc in hexanes to 80% EtOAc in hexanes) to give the product as a purple solid (0.065 g, 14%). M.p.=153-155° C.; 400 MHz $^1$H NMR (CDCl$_3$) δ: 8.43-8.35 (m, 1H), 8.33-8.24 (m, 1H), 8.05-7.94 (m, 1H), 7.72-7.56 (m, 2H), 7.56-7.4 (m, 2H), 7.33-7.2 (m, 1H), 4.98-4.86 (m, 1H), 4.54-4.34 (m, 2H), 3.34-3.16 (m, 2H); LCMS: 340 [M+H].

Synthesis of methyl 2-methyl-5,6-dioxo-2,3,5,6-tetrahydronaphtho[1,2-b][1,4]oxathiine-2-carboxylate (Compound 18)

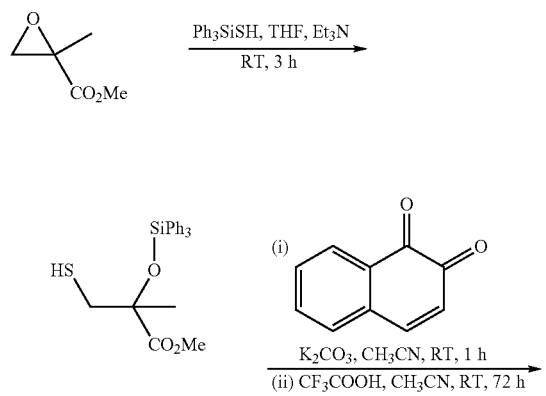

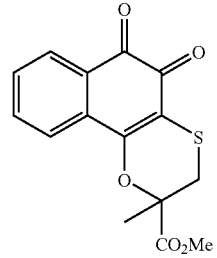

To a solution of triphenylsilanethiol (4.987 g, 17.05 mmole) in THF (50 mL) was added the methyl 2-methyloxirane-2-carboxylate (1.64 mL, 15.5 mmol) followed by triethylamine (2.6 mL, 18.6 mmol). The reaction mixture was stirred at room temperature for 3 hours. The solvent was removed under reduced pressure to give the desired product methyl 3-mercapto-2-methyl-2-[(triphenylsilyl)oxy]propanoate as a yellow oil, which was used directly in the next step without purification. The crude methyl 3-mercapto-2-methyl-2-[(triphenylsilyl)oxy]propanoate was dissolved in acetonitrile (200 mL) and treated with the naphthalene-1,2-dione (2.4 g, 15.5 mmole) and potassium carbonate (6.2 g). The reaction mixture was stirred at room temperature for one hour after which the reaction mixture was filtered to remove the potassium carbonate. To the resulting acetonitrile solution obtained after filtration was added trifluoroacetic acid (60 mL) and the mixture was stirred at room temperature for 72 hours. The solvent was then removed under reduced pressure. The resulting residue was dissolved in dichloromethane (200 mL) and washed successively with water (50 mL), saturated sodium carbonate solution (2×50 mL), water (50 mL) and saturated sodium chloride solution (50 mL). The organic extract was dried over magnesium sulfate and concentrated under reduced pressure. The crude mixture was purified by flash chromatography (SiO$_2$, 100% dichloromethane) to give the desired product, methyl 2-methyl-5,6-dioxo-2,3,5,6-tetrahydronaphtho[1,2-b][1,4]oxathiine-2-carboxylate (0.42 g, 9% for three steps) as a dark red solid. M.p.=188-189° C.; 400 MHz $^1$H NMR (CDCl$_3$) δ: 8.06 (dd, J=7.7, 1.1 Hz, 1H), 7.82 (dd, J=7.7, 0.9 Hz, 1H), 7.67 (td, J=7.7, 1.1 Hz, 1H), 7.50 (td, J=7.6, 1.1 Hz, 1H), 3.81 (s, 3H), 3.38 (d, J=13.2 Hz, 1H), 3.04 (d, J=13.7 Hz, 1H), 1.88 (s, 3H); LCMS: 305 [M+H]; Calc. for C$_{15}$H$_{12}$O$_5$S: C, 59.20; H, 3.97; N, 0. Found C, 59.52; H, 4.04; N, 0.05.

Synthesis of isopropyl 2-methyl-5,6-dioxo-2,3,5,6-tetrahydronaphtho[1,2-b][1,4]oxathiine-2-carboxylate (Compound 19)

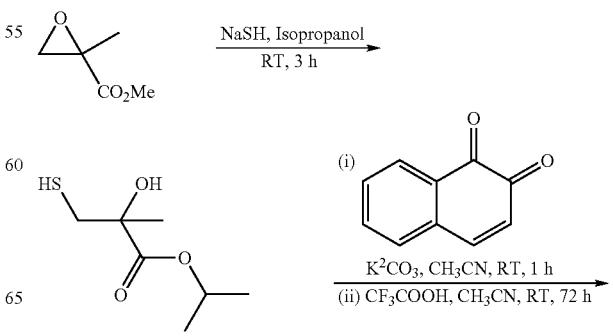

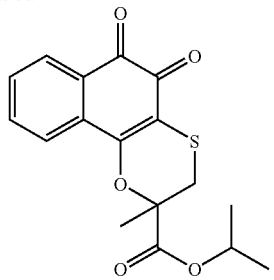

To round bottom flask containing sodium hydrosulfide (0.582 g, 10.4 mmol) in isopropanol (20 mL) was added methyl 2-methyloxirane-2-carboxylate (1.0 mL, 9.44 mmol). The reaction mixture was stirred at room temperature for 2.5 hours. To the reaction mixture was then added water (20 ml) and the pH adjusted to 2 with 2 N HCl. The reaction mixture was extracted with diethyl ether (3×50 mL). The organic extracts were combined, dried with sodium sulfate and concentrated under reduced pressure. The resulting crude isopropyl 3-mercapto-2-methyl-2-propanoate obtained was used in the next reaction with naphthalene-1,2-dione trifluoroacetic acid as outlined for example 21. The final desired product isopropyl 2-methyl-5,6-dioxo-2,3,5,6-tetrahydronaphtho[1,2-b][1,4]oxathiine-2-carboxylate was obtained as a dark red solid (overall yield 5% for the three steps). M.p.=168-169° C.; 400 MHz $^1$H NMR (CDCl$_3$) δ: 8.06 (dd, J=7.7, 1.1 Hz, 1H), 7.83 (dd, J=7.7, 0.9 Hz, 1H), 7.66 (td, J=7.7, 1.4 Hz, 1H), 7.49 (td, J=7.5, 1.1 Hz, 1H), 5.08 (septuplet, J=6.3 Hz, 1H), 3.35 (d, J=13.2 Hz, 1H), 3.03 (d, J=13.2 Hz, 1H), 1.86 (s, 3H), 1.27 (d, J=6.3 Hz, 3H), 1.26 (d, J=6.3 Hz, 3H); LCMS: 333 [M+H]; Calc. for C$_{17}$H$_{16}$O$_5$S: C, 61.43; H, 4.85; N, 0. Found C, 61.93; H, 4.92; N, 0.04.

Example 5

Antiproliferative Activity

Compounds of the present invention have demonstrated potent antiproliferative activity against a variety of cancer cell lines, including DLD-1 and HT-29 human colon carcinoma cells; A549 human lung carcinoma cells; DU-145 human prostate carcinoma cells; K-562 human leukemia cells; and PACA-2 human pancreatic carcinoma cells. Since β-lapachone induces cell death only in cancer cell lines and not in normal cells (Li et al., (2003) Proc Natl Acad Sci USA. 100 (5): 2674-8), the present compounds were also tested in a panel of normal cell lines from a variety of tissues including NCM-460 normal colon epithelial cells.

Table 1 shows the concentrations of the compounds required to inhibit 50% of cell growth (IC$_{50}$). As shown in Table 1, IC$_{50}$ values in the low micromolar range and below were obtained for several of these compounds in all cancer cell lines tested.

Another effect of the compounds of the present invention is the induction or elevation of activity (e.g. elevation of the level) of one or more checkpoint molecules (i.e., a member of the E2F family of transcription factors). Studies have shown that β-lapachone induces activation of E2F1 checkpoint pathway in nuclei of cancer cells but not in normal cells, resulting in the arrest of cancer cells in G1 and/or S phase. Several compounds of the present invention were effective in activating the E2F1 checkpoint pathway, thus causing G1 and/or S phase arrest. Furthermore, the compounds of the present invention have no significant toxic effects on normal cells (See, Table 1).

Table 1.

TABLE 1

| | IC$_{50}$ Values (μM) | | | | | | |
|---|---|---|---|---|---|---|---|
| | Cancerous Cells | | | | | Normal Cells | Fold Selectivity |
| Compound No. | Lung A549 | Colon DLD-1 | Prostate DU-145 | Leukemia K-562 | Pancreas PACA-2 | Colon NCM-460 | (NCM-460/DLD1) |
| 1 | 4.77 | 1.84 | 4.01 | 2.93 | 1.95 | 4.78 | 2.6 |
| 2 | 11.7 | 2.05 | 3.88 | 2.84 | 1.64 | 10.8 | 5.3 |
| 5 | 4.79 | 1.57 | 1.49 | 2.68 | 1.34 | 9.83 | 6.3 |
| 6 | 12.9 | 4.01 | 4.67 | 5.29 | 3.78 | 17.1 | 4.3 |
| 7 | 11.3 | 2.95 | 4.22 | 3.89 | 2.75 | 11.4 | 3.9 |
| 11 | 5.44 | 1.36 | 4.05 | 2.73 | 2.05 | 7.65 | 5.6 |
| 12 | 4.66 | 2.17 | 3.72 | 1.51 | 1.68 | 5.92 | 2.7 |
| 13 | >100 | 12.9 | 13.2 | 10.9 | 12.1 | 18.6 | 1.4 |
| 14 | >100 | 3.8 | 3.79 | 4.61 | 3.39 | 10.1 | 2.7 |
| 15 | >100 | 32.8 | >100 | 58.2 | 32.4 | 33.6 | 1.0 |
| 17 | 5.08 | 2.39 | 3.82 | 2.89 | 2.04 | 5.61 | 2.3 |

Cell viability was determined by measuring the activity of dehydrogenase enzymes in metabolically active cells using a tetrazolium compound, MTS. The assay was performed as described in Promega Technical Bulletin No. 169 (CellTiter 96 Aqueous Non-Radioactive Cell Proliferation Assay): All cells lines were grown in DMEM media (4.5 g/L glucose) supplemented with 15% heat-inactivated FBS, 10 mM L-glutamine, and 10 mM HEPES. Briefly, cells were seeded in 96-well plates and incubated for 16 to 24 hours; test compounds were serially diluted in DMSO, further diluted in cell culture media, then added to cells (final DMSO concentration of 0.33% v/v); cells were incubated in the presence of compound for 4 hours; MTS was added to the cells and incubated for four hours; SDS was added to a final concentration of 1.4% v/v and absorbance at 490 nM was measured within two hours using a plate reader. The amount of 490 nM absorbance was directly proportional to the number of living cells in the culture. The IC$_{50}$ was defined as the concentration of compound that results in a 50% reduction in the number of viable cells as compared to control wells treated with DMSO only (0.33% v/v) and 1.4% v/v SDS, and was calculated using non-linear regression analysis within Activitybase software suite.

The assays of the present invention as shown in Table 1 and methods of measuring induction of E2F1 activity and elevation of E2F1 levels can be carried out following the descriptions found in Li et al., (2003) *Proc Natl Acad Sci USA*. 100(5): 2674-8 and U.S. Patent Application Publication No. 2002/0169135, both incorporated herein by reference.

The antiproliferative activity of the present dihydro-oxathiine naphthoquinone derivative compounds suggests that compounds of the present invention may show wide anticancer activity. For example, the compounds of the invention are effective for treating cancers such as colon, lung, prostate, leukemia, and pancreas. These treatments are accomplished utilizing the present dihydro-oxathiine naphthoquinone derivative compounds, alone or can be utilized in combination with, other chemotherapy agents or with radiation therapy. For example, the compounds of the present invention are used for the prevention or treatment of a hyperproliferative disorder and cancer (e.g., as a preventative drug) by preventing hyperproliferative or cancer cell formation. The results of experiments with β-lapachone and similar chemical compounds have shown that the compounds of the present invention have a cell death effect on a variety of human cancer cells and that they can inhibit growth of other human cancer cells.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:
1. A compound of Formula I:

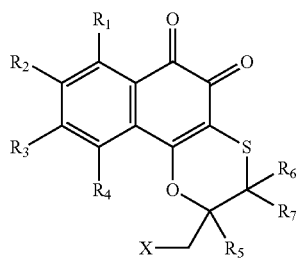

(I)

or a pharmaceutically acceptable salt and/or an individual diastereomer thereof, wherein:
$R_1$, $R_2$, $R_3$, and $R_4$ are each, independently, H, halogen, hydroxyl, unsubstituted or substituted $C_1$-$C_6$ alkyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, or amide;
$R_5$ is H, or carboxyacid, or carboxy esters;
$R_6$ and $R_7$ are each, independently, H, unsubstituted or substituted $C_1$-$C_6$ alkyl, unsubstituted or substituted $C_1$-$C_6$ alkenyl, unsubstituted and substituted $C_1$-$C_6$ alkoxy, unsubstituted or substituted $C_1$-$C_6$ acyl, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle;
X is H, —$OR_a$, unsubstituted or substituted alkylamino; unsubstituted or substituted dialkylamino, or substituted heterocycle;
$R_a$ is H, unsubstituted or substituted amide, unsubstituted or substituted heterocycle, or substituted silyl; provided that
if X is —$OR_a$ and $R_a$ and $R_1$-$R_5$ are each H, then $R_6$ and $R_7$ are not both H;
if X and $R_1$-$R_6$ are each H, then $R_7$ is not methyl; and
if X, $R_1$-$R_5$ and $R_7$ are each H, then $R_6$ is not methyl.

2. A compound of Formula II:

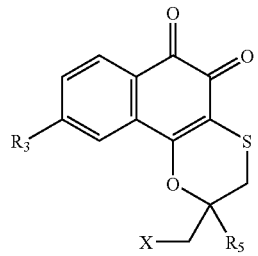

(II)

or a pharmaceutically acceptable salt and/or an individual diastereomer thereof, wherein:
$R_3$ is H, halogen, unsubstituted or substituted aryl, unsubstituted or substituted phenyl, unsubstituted or substituted heteroaryl, or unsubstituted or substituted heterocycle;
$R_5$ is H, carboxyacid, or carboxy esters;
X is H, —$OR_a$, unsubstituted or substituted alkylamino, unsubstituted or substituted dialkylamino, or substituted heterocycle;
$R_a$ is H, unsubstituted or substituted amide, unsubstituted or substituted heterocycle, or substituted silyl; provided that
if X is —$OR_a$ and $R_a$ and $R_1$-$R_5$ are each H, then $R_6$ and $R_7$ are not both H;
if X and $R_1$-$R_6$ are each H, then $R_7$ is not methyl; and
if X, $R_1$-$R_5$ and $R_7$ are each H, then $R_6$ is not methyl.

3. The compound of claim 2, wherein X is substituted heterocycle.

4. The compound of claim 3, wherein the heterocycle is piperazine or piperidine.

5. The compound of claim 3, wherein the heterocycle is substituted with one of the following:
(a) carbonylalkoxy;
(b) carboxyacid;
(c) phenyl;
(d) heteroaryl;
(e) heterocycle;
(f) hydroxyl;
(g) acetal; or
(h) $C_1$-$C_6$ alkyl;
each of which may be substituted.

6. The compound of claim 5, wherein the heterocycle is substituted with carbonylalkoxy.

7. The compound of claim 6, wherein the carbonylalkoxy is

[chemical structure showing C(=O)OCH$_2$CH$_3$]

8. The compound of claim 5, wherein the heterocycle is substituted at the 4-position.

9. The compound of claim 5, wherein the heterocycle is substituted with hydroxyl.

10. The compound of claim 5, wherein the heterocycle is substituted with substituted $C_1$-$C_6$ straight chain alkyl.

11. The compound of claim 10, wherein the substituted $C_1$-$C_6$ straight chain alkyl is —CH$_2$W, wherein:
W is hydroxyl, alkoxy, or —C(O)NR$_8$R$_9$;
R$_8$ is H or $C_1$-$C_6$ straight chain alkyl; and
R$_9$ is $C_1$-$C_6$ straight chain alkyl, $C_3$-$C_6$ branched alkyl, or $C_3$-$C_6$ cycloalkyl.

12. The compound of claim 11, wherein W is hydroxyl.

13. The compound of claim 11, wherein W is —C(O)NR$_8$R$_9$.

14. The compound of claim 13, wherein R$_8$ is H and R$_9$ is isopropyl.

15. The compound of claim 5, wherein the heterocycle is substituted with substituted phenyl.

16. The compound of claim 15, wherein the phenyl is substituted with at least one halogen.

17. The compound of claim 16, wherein the phenyl is substituted with F.

18. The compound of claim 5, wherein the heterocycle is substituted with acetal.

19. The compound of claim 18, wherein the acetal is cyclic acetal.

20. The compound of claim 2, wherein X is —OR$_a$.

21. The compound of claim 20, wherein R$_a$ is substituted amide.

22. The compound of claim 21, wherein the substituted amide is —C(O)NR$_{10}$R$_{11}$; and
R$_{10}$ and R$_{11}$ are the same or different from each other and each represents:
(a) H;
(b) unsubstituted or substituted phenyl;
(c) unsubstituted or substituted aryl;
(d) methyl;
(e) unsubstituted or substituted $C_2$-$C_6$ straight chain alkyl;
(f) unsubstituted or substituted $C_3$-$C_6$ branched alkyl;
(g) unsubstituted or substituted $C_3$-$C_8$ cycloalkyl;
(f) unsubstituted or substituted $C_3$-$C_6$ alkenyl;
(h) unsubstituted or substituted heterocycle; or
(i) unsubstituted or substituted heteroaryl.

23. The compound of claim 22, wherein R$_{10}$ is H and R$_{11}$ is unsubstituted phenyl.

24. The compound of claim 22, wherein R$_{10}$ is H and R$_{11}$ is substituted phenyl.

25. The compound of claim 24, wherein the phenyl is substituted with one or more groups selected from: halogen, hydroxyl, methyl, —CF$_3$, $C_2$-$C_6$ straight chain alkyl, $C_3$-$C_6$ branched alkyl, $C_3$-$C_8$ cycloalkyl, nitro, cyano, amino, alkylamino, dialkylamino, alkoxy, —OCF$_3$, carboxyacid, carbonylalkyl, carbonylalkoxy, thio, thioalkyl, phenyl, aryl, heterocycle, and heteroaryl.

26. The compound of claim 25, wherein the phenyl is substituted with halogen, hydroxyl, —CF$_3$, nitro, cyano, or alkoxy.

27. The compound of claim 26, wherein the phenyl is substituted with at least one halogen.

28. The compound of claim 27, wherein the halogen is F.

29. The compound of claim 22, wherein R$_{10}$ is H and R$_{11}$ is $C_3$-$C_6$ branched alkyl.

30. The compound of claim 29, wherein the branched alkyl is isopropyl.

31. The compound of claim 20, wherein R$_a$ is R$^x$R$^y$R$^z$Si—, wherein R$^x$, R$^y$, and R$^z$ are the same or different from each other and each represents methyl, ethyl, i-propyl, t-butyl, or phenyl.

32. The compound of claim 31, wherein R$^x$ and R$^y$ are each phenyl and R$^z$ is t-butyl.

33. The compound of claim 20, wherein R$_a$ is unsubstituted or substituted heterocycle.

34. The compound of claim 33, wherein the heterocycle is pyridine.

35. The compound of claim 34, wherein the pyridine is 3-pyridine.

36. The compound of claim 2, wherein R$_3$ is unsubstituted or substituted phenyl or unsubstituted or substituted heterocycle.

37. The compound of claim 36, wherein R$_3$ is unsubstituted phenyl.

38. The compound of claim 36, wherein R$_3$ is unsubstituted heterocycle.

39. The compound of claim 38, wherein the heterocycle is piperidine.

40. The compound of claim 36, wherein R$_5$ and X are each H.

41. The compound of claim 2, wherein X is H.

42. The compound of claim 41, wherein R$_5$ is carboxyacid.

43. The compound of claim 41, wherein R$_5$ is H.

44. The compound of claim 2, wherein X is alkylamino or dialkylamino, each of which may be substituted.

45. The compound of claim 44, wherein the alkylamino or the dialkylamino is —NR$_{12}$R$_{13}$; and R$_{12}$ and R$_{13}$ are each independently H, unsubstituted or substituted $C_1$-$C_6$ straight chain alkyl, $C_3$-$C_6$ branched alkyl, or unsubstituted or substituted benzyl.

46. The compound of claim 45, wherein R$_{12}$ is H and R$_{13}$ is unsubstituted benzyl.

47. The compound of claim 45, wherein R$_{12}$ is H and R$_{13}$ is substituted $C_1$-$C_6$ straight chain alkyl.

48. The compound of claim 47, wherein R$_{13}$ is ethylphenyl.

49. The compound of claim 45, wherein R$_{12}$ is substituted $C_1$-$C_6$ straight chain alkyl.

50. The compound of claim 49, wherein the alkyl is substituted with acetal.

51. The compound of claim 45, wherein R$_{13}$ is methyl.

52. A compound of Formula III:

[chemical structure of Formula (III) showing a naphthoquinone-type structure with substituents R$_1$, R$_2$, R$_3$, R$_4$ on one ring, S, R$_{19}$, R$_{18}$, R$_{17}$, R$_{16}$, R$_{15}$, R$_{14}$, and O]

or a pharmaceutically acceptable salt and/or an individual diastereomer thereof, wherein:

$R_1$, $R_2$, $R_3$, $R_4$, $R_{14}$, $R_{15}$, $R_{16}$, $R_{17}$, $R_{18}$, and $R_{19}$ are each, independently, H, halogen, hydroxyl, unsubstituted or substituted $C_1$-$C_6$ alkyl, unsubstituted or substituted —$C_2$-$C_6$alkenyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, amide, unsubstituted or substituted $C_1$-$C_6$ acyl, or $C_1$-$C_6$ alkoxycarbonyl.

53. The compound of claim 52, wherein $R_{19}$ is unsubstituted or substituted $C_1$-$C_6$ alkyl.

54. The compound of claim 53, wherein $R_{19}$ is propyl.

55. A pharmaceutical composition comprising a therapeutically effective amount of a compound of claim 1 in combination with a pharmaceutically acceptable carrier.

56. A pharmaceutical composition comprising a therapeutically effective amount of a compound of claim 2 in combination with a pharmaceutically acceptable carrier.

57. A pharmaceutical composition comprising a therapeutically effective amount of a compound of claim 52 in combination with a pharmaceutically acceptable carrier.

* * * * *